United States Patent
Shidara

(10) Patent No.: US 8,313,425 B2
(45) Date of Patent: Nov. 20, 2012

(54) APPARATUS AND METHOD FOR MEASURING DISPLACEMENT AMOUNT OF ENDOSCOPE IMAGE, ELECTRONIC ENDOSCOPE, AND IMAGE PROCESSING DEVICE FOR ENDOSCOPE

(75) Inventor: Kenichi Shidara, Kanagawa (JP)

(73) Assignee: Fujifilm Corporation, Tokyo (JP)

( * ) Notice: Subject to any disclaimer, the term of this patent is extended or adjusted under 35 U.S.C. 154(b) by 589 days.

(21) Appl. No.: 12/544,003

(22) Filed: Aug. 19, 2009

(65) Prior Publication Data

US 2010/0048993 A1    Feb. 25, 2010

(30) Foreign Application Priority Data

Aug. 21, 2008  (JP) .................... 2008-213107

(51) Int. Cl.
*A61B 1/04*    (2006.01)
(52) U.S. Cl. ........................................ 600/109
(58) Field of Classification Search .............. 600/109
See application file for complete search history.

(56) References Cited

U.S. PATENT DOCUMENTS

| | | | | |
|---|---|---|---|---|
| 5,820,547 A * | 10/1998 | Strobl et al. | ................. | 600/127 |
| 5,841,525 A * | 11/1998 | Rosow et al. | ................. | 356/124.5 |
| 6,190,308 B1 * | 2/2001 | Irion et al. | ................. | 600/109 |
| 6,833,912 B2 * | 12/2004 | Lei et al. | ................. | 356/124 |
| 7,486,805 B2 * | 2/2009 | Krattiger | ................. | 382/108 |
| 7,892,165 B2 * | 2/2011 | Nakamura | ................. | 600/117 |
| 2002/0057345 A1 * | 5/2002 | Tamaki et al. | ................. | 348/207 |
| 2007/0035797 A1 * | 2/2007 | Kanai | ................. | 359/212 |

FOREIGN PATENT DOCUMENTS

| | | |
|---|---|---|
| JP | 10-28233 | 1/1998 |
| JP | 11-290269 | 10/1999 |
| JP | 2001-86378 | 3/2001 |
| JP | 2008-104877 (A) | 5/2008 |

OTHER PUBLICATIONS

Japanese Office Action dated Sep. 10, 2012, with English translation.

* cited by examiner

*Primary Examiner* — Rodney Fuller
(74) *Attorney, Agent, or Firm* — McGinn IP Law Group, PLLC

(57) ABSTRACT

An image of a test chart having a test pattern is taken with an electronic endoscope. A DSP of a processing device generates a test pattern image from image signals input from the electronic endoscope. An image compositor composites the test pattern image and a test mask image having a predetermined reference pattern and generates a test mask composite image. An inspector visually measures positional and rotational displacement amounts of the test pattern with respect to the reference pattern in the test mask composite image displayed on a monitor, and inputs measurement results as displacement amount information to the processing device. The displacement amount information is stored in an EEPROM of the electronic endoscope. The processing device calibrates an endoscope image of a body cavity based on the displacement amount information input from the electronic endoscope.

19 Claims, 16 Drawing Sheets

FIG. 4A  FIG. 4B
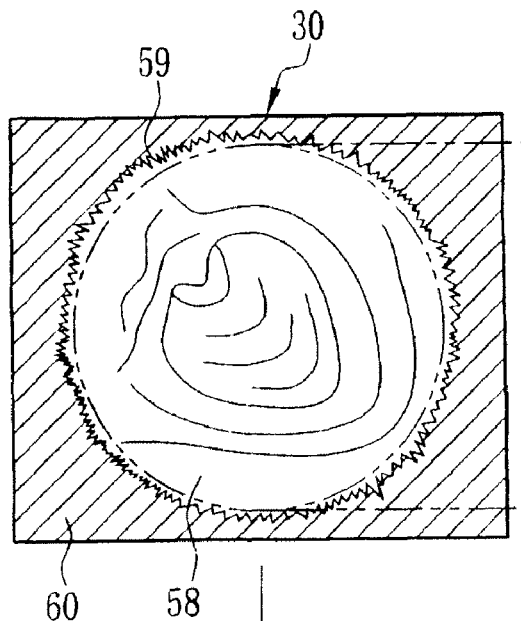
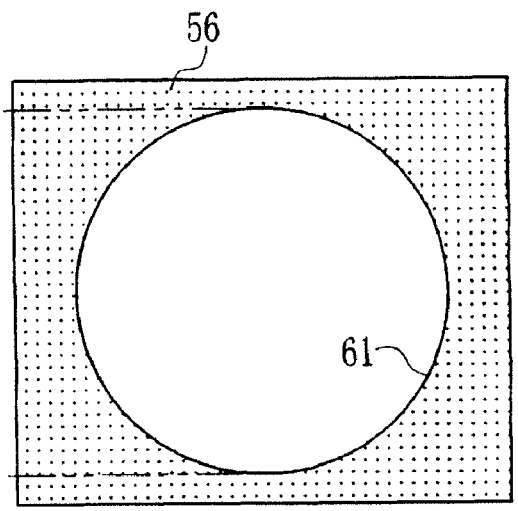
FIG. 4C
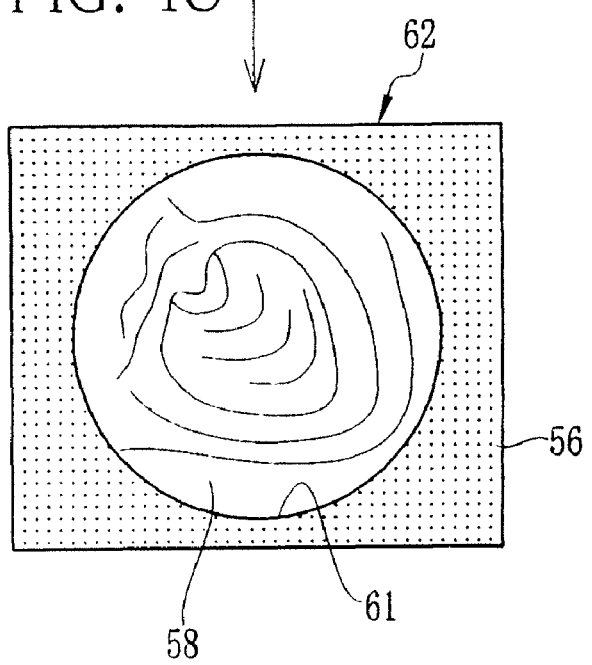

FIG. 5A
FIG. 5B
(A) 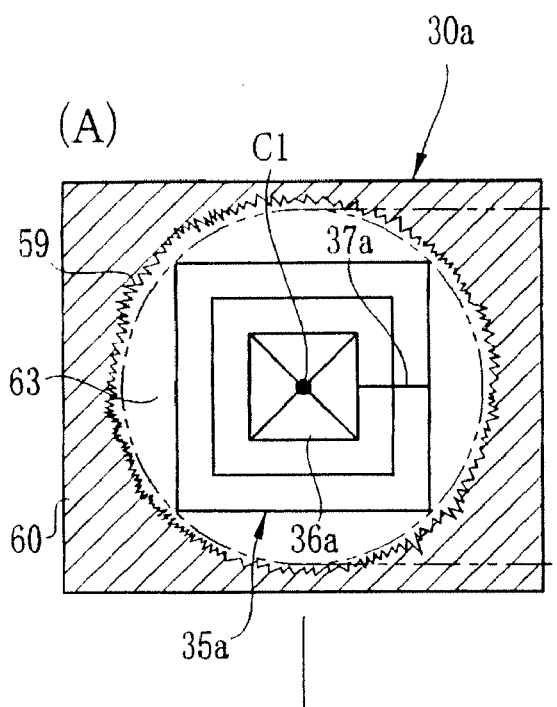
(B) 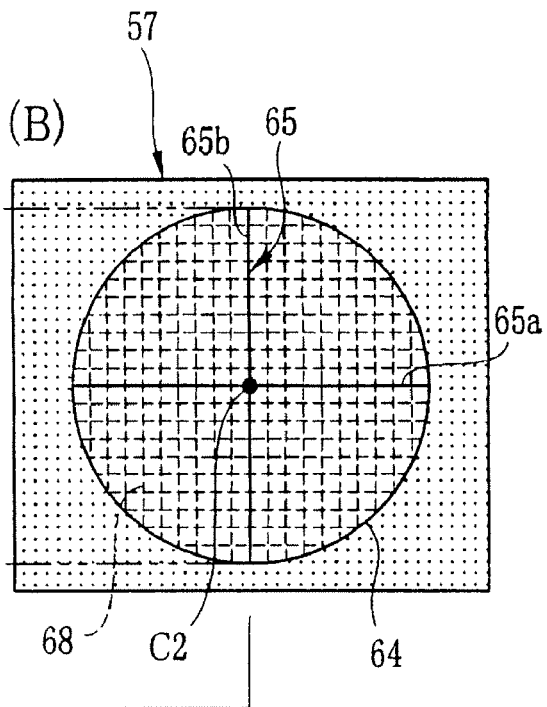
FIG. 5C
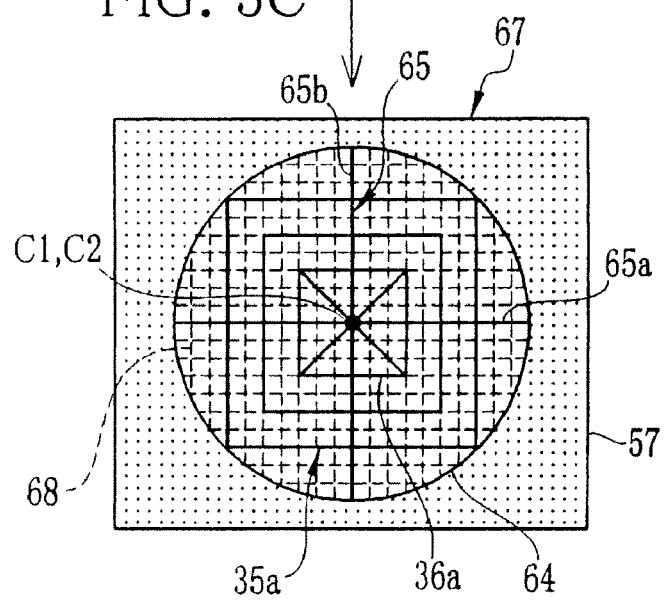

APPARATUS AND METHOD FOR MEASURING DISPLACEMENT AMOUNT OF ENDOSCOPE IMAGE, ELECTRONIC ENDOSCOPE, AND IMAGE PROCESSING DEVICE FOR ENDOSCOPE

FIELD OF THE INVENTION

The present invention relates to an electronic endoscope, an image processing device for performing image processing to an endoscope image obtained with this electronic endoscope, and an apparatus and a method for measuring a displacement amount of the endoscope image.

BACKGROUND OF THE INVENTION

Electronic endoscope systems are widely used in medical diagnoses. An electronic endoscope system is composed of an electronic endoscope having an insert section to be inserted in a body cavity of a patient and a processing device connected to this electronic endoscope. The processing device generates an endoscope image based on image signals received from an image sensor mounted to a distal portion of the insert section of the electronic endoscope. The processing device performs image processing to the endoscope image, and then outputs the endoscope image to a monitor. A doctor observes the body cavity and makes diagnosis, or treats the patient using a medical instrument projected from a medical instrument outlet of the distal portion of the insert section while viewing the endoscope image displayed on the monitor.

When the image sensor mounted to the distal portion of the insert section is positionally displaced from its correct mounting location, and/or rotationally displaced from its correct mounting orientation, the endoscope image displayed on the monitor is also positionally and/or rotationally displaced. As a result, the medical instrument projected from the medical instrument outlet is not displayed in a normal position on the monitor, making the endoscope awkward to use. Moreover, endoscopes, regardless of optical or digital type, have achieved high zoom magnification due to increase in the number of pixels in the image sensor. When the endoscope zooms in with its image sensor displaced from the center, the displacement amount of the image from the center also increases. As a result, the zoomed area is displaced from the intended area, which also makes the endoscope awkward to use. Thus, improvement on mounting location accuracy of the image sensor is required so as to reduce the displacement amount under higher magnification. In addition, a diameter of the endoscope is becoming smaller and smaller to reduce physical burden on a patient. Accordingly, the size of the image sensor is reduced and pixels are arranged at high densities with narrower spacing, increasing the displacement amount on the light receiving surface of the image sensor even though the mechanical displacement amount is unchanged. Thus, it is required to align the image sensor with the correct mounting location with a high degree of accuracy.

To solve the above-described problems, an imaging device for an endoscope according to Japanese Patent Laid-Open Publication No. 10-028233 has a position adjustment mechanism for adjusting a position of an image sensor mounted to a distal portion of an insert section in horizontal, vertical, and rotational directions. With the use of this position adjustment mechanism, the image sensor is aligned with a correct mounting location and orientation.

Japanese Patent Laid-Open Publication No. 11-290269 discloses a solid state imaging device for positioning and fixing an objective lens group forward of an image sensor. By utilizing this art for positioning and fixing the image sensor, the image sensor is aligned with a correct mounting location and orientation. An electronic endoscope disclosed in Japanese Patent Laid-Open Publication No. 2001-086378 has a fixing frame (see the fourth example) for positioning the image sensor. With the use of the fixing frame, the image sensor is aligned with a correct mounting location and orientation.

In the above publications No. 10-028233, 11-290269, and 2001-086378, the image sensor is aligned using the mechanical structures. Therefore, the mounting location accuracy of the image sensor is easily improved, although it has limitations. When the number of pixels in the image sensor further increases, the mechanical structures disclosed in the above publications may not be able to cope with the improvement on zooming alignment required due to the higher magnification of the electronic zoom, and improvement on the mounting location accuracy required due to downsizing of the image sensor in an electronic endoscope with a smaller diameter. In particular, in Japanese Patent Laid-Open Publication No. 10-028233, an inspector manually carries out the alignment using the position adjustment mechanism. Therefore, the mounting location accuracy of the image sensor depends on the skill of the inspector. In addition, in the above publications No. 10-028233, 11-290269, and 2001-086378, the mechanical structures increase production costs.

SUMMARY OF THE INVENTION

In view of the foregoing, an object of the present invention is to provide an apparatus and a method for measuring a displacement amount of an endoscope image, electronic endoscope, and an image processing device for this electronic endoscope that enables calibration of the endoscope image without using mechanical structure.

In order to achieve the above and other objects, an apparatus for measuring a displacement amount of an endoscope image according to the invention includes a test chart having a test pattern, an alignment section, an image compositor, and a displacement amount obtaining section. The alignment section aligns one of a distal portion of an insert section of an electronic endoscope and the test chart with the other such that the distal portion opposes the test chart and is located in a predetermined circumferential position. The distal portion is to be inserted into a body cavity. A test pattern image is obtained by taking an image of the test chart with the electronic endoscope after the alignment. The image compositor generates a composite image from the test pattern image and a reference image having a reference pattern. The reference pattern indicates a reference position and a reference orientation of the test pattern. The displacement amount obtaining section obtains a displacement amount of the test pattern with respect to the reference pattern in the composite image as the displacement amount of the endoscope image.

It is preferable that the test pattern has a chart alignment mark indicating at least one point on the test chart, and an orientation detection mark for detecting an orientation of the test chart. It is preferable that the reference pattern has a reference position mark indicating at least one point on the reference image and a reference orientation mark. The reference position mark coincides with the chart alignment mark and the reference orientation mark overlaps with the orientation detection mark when the displacement amount is zero. It is preferable that the displacement amount obtaining section obtains a positional displacement amount and a rotational displacement amount as the displacement amount. The positional displacement amount is a distance between the chart alignment mark and the reference position mark. The rotational displacement amount is an angle between a first line and a second line. The first line passes the chart alignment mark and the orientation detection mark, and the second line passes the reference position mark and the reference orientation mark.

It is preferable that the test pattern is a checkered pattern of at least two colors arranged alternately, and the chart alignment mark is an intersection point of blocks in the checkered pattern, and the orientation detection mark is a line of one of the blocks.

It is preferable that the chart alignment mark is a first dot of a first color, and the orientation detection mark is a second dot of a second color different from the first color.

It is preferable that the reference image has a scale line to obtain virtual position coordinates of the chart alignment mark and the orientation detection mark in the composite image. With the use of the scale line, the displacement amount is visually measured.

It is preferable that the apparatus further includes a display section for displaying the composite image, and an input terminal for inputting the position coordinates or the displacement amount calculated from the position coordinates. It is preferable that the displacement amount obtaining section obtains the position coordinates or the displacement amount input through the input terminal.

It is preferable that the displacement amount obtaining section analyzes the composite image and obtains the displacement amount by automatic measurement. By automatically measuring the displacement amount, burdens of an inspector is reduced, and the displacement amount is measured in a short time.

It is preferable that the displacement amount obtaining section reads the colors of the blocks in the composite image, and detects an area of each of the read color. It is preferable that the displacement amount obtaining section automatically measures the displacement amount based on the intersection point of the blocks, the line of one of the blocks, and positions of the reference position mark and the reference orientation mark.

It is preferable that the displacement amount obtaining section reads the first color and the second color in the composite image and detects positions of the first dot and the second dot based on the reading. It is preferable that the displacement amount obtaining section automatically measures the displacement amount based on positions of the first dot, the second dot, the reference position mark and the reference orientation mark.

It is preferable that the chart alignment mark indicates a center position of the test chart, and the reference position mark indicates a center position of the reference image.

It is preferable that the apparatus further includes a displacement correcting section for correcting the displacement of the endoscope image to reduce the displacement amount obtained by the displacement amount obtaining section to zero.

It is preferable that the displacement amount obtaining section obtains the angle, after obtaining the positional displacement amount and the displacement correcting section reduces the positional displacement amount to zero.

It is preferable that the apparatus further includes a displacement amount outputting section for outputting the displacement amount, obtained by the displacement amount obtaining section, to an external memory device.

It is preferable that the reference image is a mask image for hiding a useless area of the endoscope image, and the mask image has an unmasked area to expose an area of the endoscope image other than the useless area. The reference pattern is provided in the unmasked area.

It is preferable that the alignment section further includes a stage onto which the test chart is placed, an approximately L-shaped holder attached to the stage, and a setting hole formed through the holder. The distal portion is inserted into the setting hole. The setting hole rotatably holds the distal portion such that a center of an image sensor of the endoscope and a center of the test pattern coincide with each other when the image sensor is in a correct mounting location.

It is preferable that the apparatus for measuring the displacement amount of the endoscope image further includes a pointer detachably attached to the distal portion and insertable in the setting hole. The pointer projects point light along a virtual circle around a center axis of the distal portion. A positioning mark is formed on the test chart. The point light is aligned with the positioning mark when the pointer is rotated together with the distal portion in the setting hole.

It is preferable that the alignment section further includes a tube-like adaptor detachably attached to the distal portion and a rod. The adaptor has an opening opposing the distal portion, a bottom portion positioned opposite to the opening, and at least one through hole formed through the bottom portion. The test chart is attached to the inside of the bottom portion. The rod is inserted through the through hole. An end of the rod is inserted into an opening of the distal portion. The rod is removed from the through hole after the adapter is attached to the distal portion.

An electronic endoscope of the present invention includes a memory for storing the displacement amount obtained by the displacement amount obtaining section.

An image processing device for endoscope of the present invention includes a displacement correcting section for retrieving the displacement amount from the memory of the electronic endoscope and performing displacement correction to the endoscope image. A method for measuring a displacement amount of an endoscope image includes an aligning step, a generating step, and an obtaining step. In the aligning step, a first one of a distal portion of an insert section of an electronic endoscope and a test chart is aligned with a second one thereof such that the distal portion opposes the test chart and is located in a predetermined circumferential position. The test chart has a test pattern. The distal portion is to be inserted into a body cavity. In the generating step, a composite image is generated from a test pattern image that is obtained by taking an image of the test chart with the electronic endoscope after the aligning step and a reference image having a reference pattern. The reference pattern indicates a reference position and a reference orientation of the test pattern. In the obtaining step, a displacement amount of the test pattern with respect to the reference pattern in the composite image is obtained as the displacement amount of the endoscope image.

In the present invention, a displacement amount of the test pattern with respect to the reference pattern is obtained from a composite image of the endoscope image and the reference image. Based on this displacement amount, the positional and rotational displacements of the endoscope image are corrected without providing the mechanical structure for correcting the position and orientation of the solid-state image sensor. Thus, the endoscope image with no positional and rotational displacements is obtained even if the mechanical structure cannot cope with the further increase in the number of pixels.

Since the mechanical structure is unnecessary, the production costs of the electronic endoscope are reduced. Furthermore, mounting location accuracy of the solid-state image sensor is relaxed. As a result, costs of parts used for mounting the solid-state image sensor are reduced, and production yields of the electronic endoscope are increased.

BRIEF DESCRIPTION OF THE DRAWINGS

The above and other objects and advantages of the present invention will be more apparent from the following detailed description of the preferred embodiments when read in connection with the accompanied drawings, wherein like reference numerals designate like or corresponding parts throughout the several views, and wherein:

FIG. 4A is an explanatory view of an endoscope image;

FIG. 4B is an explanatory view of a normal mask image;

FIG. 4C is an explanatory view of a normal mask composite image;

FIG. 5A is an explanatory view of an endoscope image and a test chart image;

FIG. 5B is an explanatory view of a test mask image;

FIG. 5C is an explanatory view of a test mask composite image;

DESCRIPTION OF THE PREFERRED EMBODIMENTS

Figure 1:
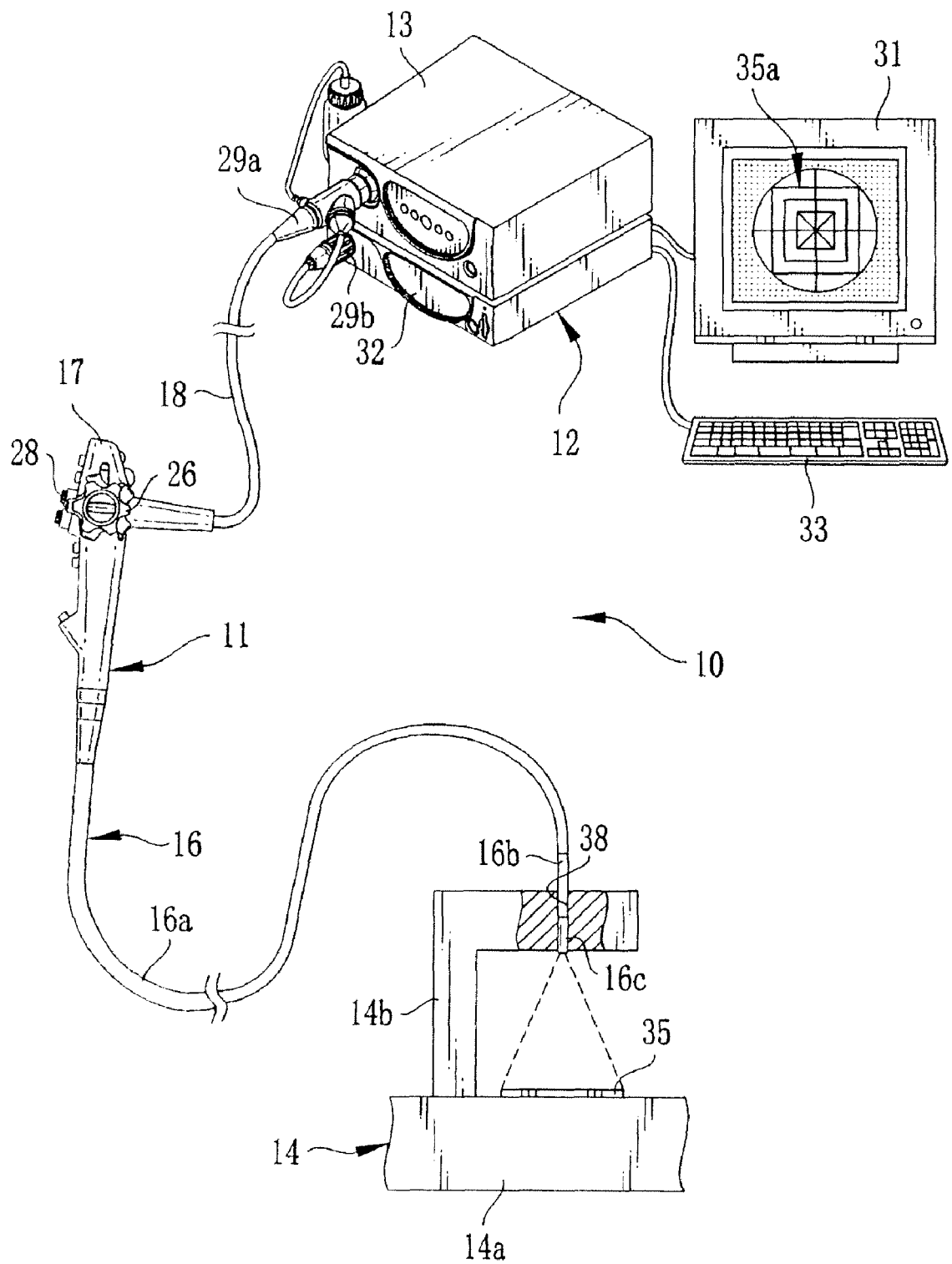
FIG. 1 is a schematic view of an electronic endoscope system of the present invention.

As shown in FIG. 1, an electronic endoscope system 10 is composed of an electronic endoscope 11, a processing device (image processing device for endoscope) 12, a light source device 13, and an endoscope alignment mechanism 14. An apparatus for measuring a displacement amount of an endoscope image according to the present invention is a calibration apparatus, and is composed of the processing device (image processing device) 12 and the endoscope alignment mechanism 14. The electronic endoscope 11 is composed of an insert section 16 to be inserted into a body cavity, an operation section 17, and a universal cord 18. The operation section 17 is used for operating the insert section 16, and also used as a grip for holding the electronic endoscope 11. The universal cord 18 is connected to the processing device 12 and the light source device 13.

The insert section 16 is a flexible rod. The insert section 16 is composed of a flexible tube 16a, a steering portion 16b, and a distal portion 16c in this order from the operation section 17 side. The flexible tube 16a occupies most of the length of the insert section 16. The steering portion 16b is bent with the operation of the operation section 17, directing the distal portion 16c to a desired direction.

Figure 16A:
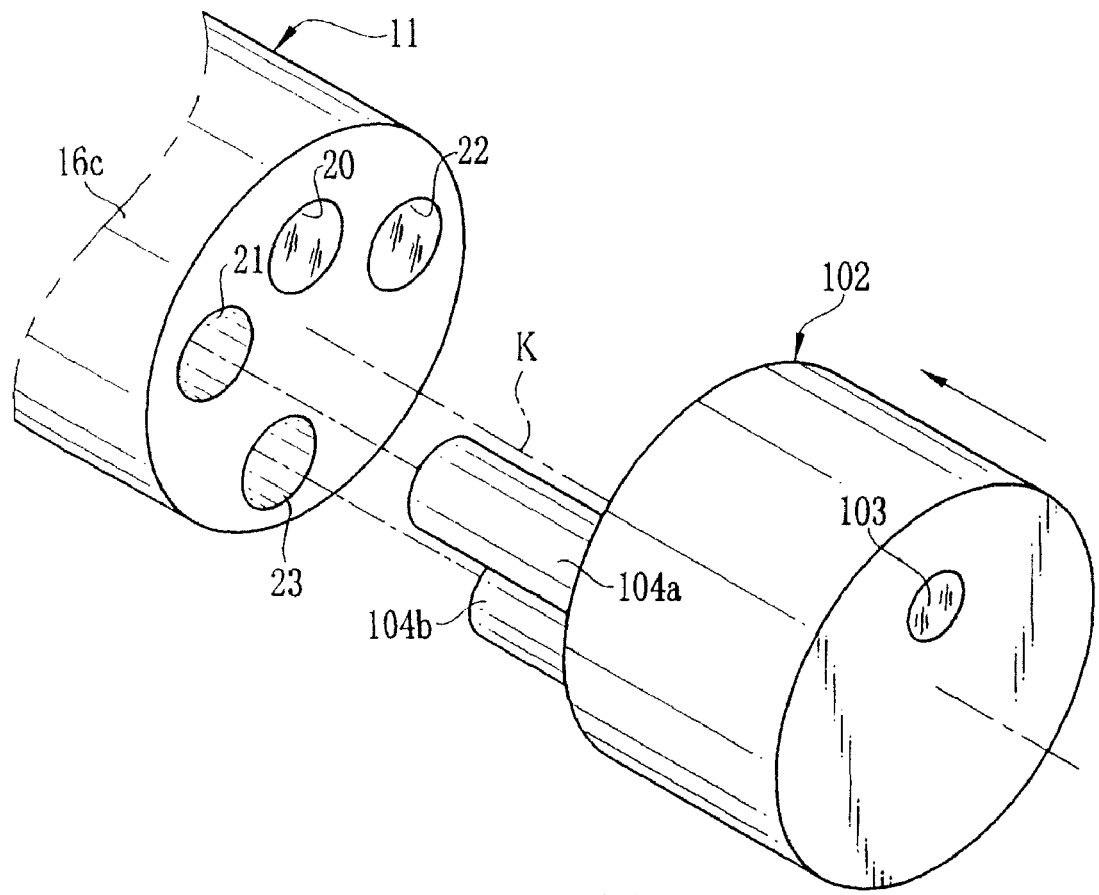
FIG. 16A is a perspective view of a pointer detached from the distal portion.

As shown in FIG. 16A, the distal portion 16c is provided with an image capturing window 20, a medical instrument outlet 21, a lighting window 22, an air/water nozzle 23. In the rear of the image capturing window 20, a CCD-type solid state image sensor (hereinafter referred to as CCD, see FIG. 3) 24 is disposed. A CMOS-type solid state image sensor may be used instead of the CCD 24.

The medical instrument outlet 21 is an end opening of a forceps channel (not shown) provided in the insert section 16. In the rear of the lighting window 22, a light guide 25 (see FIG. 3) is provided. Through the air/water nozzle 23, air and water are supplied to the image capturing window 20 and the body cavity.

The operation section 17 is provided with an angle knob 26, operation buttons 28, and the like. The angle knob 26 is rotated to adjust the direction and amount of bending of the steering portion 16b. The operation buttons 28 are used for various operations such as supplying air or water, and suction. The universal cord 18 is connected to the operation section 17.

The air/water nozzle 23, a lead for transmitting image signals, and the light guide 25 are incorporated through the universal cord 18. The universal cord 18 is provided with a connector 29a at a tip on the opposite side of the electronic endoscope 11. The connector 29a is connected to the light source device 13. This light source device 13 has a light source that supplies illumination light to the light guide 25. A sub-connector 29b branches off from the connector 29a, and is connected to the processing device 12.

The processing device 12 generates an endoscope image 30 (see FIG. 4) from image signals input from the CCD 24, and performs image processing to the endoscope image 30.

Thereafter, the endoscope image 30 is displayed on a monitor 31 connected to the processing device 12 via a cable.

A front panel 32 is provided on a front face of the processing device 12. The front panel 32 has operation buttons for displaying a desired menu screen on the monitor 31 and changing image processing settings such as contrast and color, and a mode changing switch for changing operation modes of the processing device 12. A keyboard (input terminal) 33 is connected to the processing device 12.

The operation modes of the processing device 12 include a displacement measuring mode in addition to a normal mode selected for observing the body cavity with the electronic endoscope 11. In the displacement measuring mode, a positional displacement amount of a test chart image 35a from a predetermined reference position and a rotational displacement amount of the test chart image 35a from a predetermined reference orientation are measured. The test chart image 35a is an image of a test chart 35 taken with the electronic endoscope 11. The reference position and the reference orientation of the test chart image 35a are the position and the orientation of the test chart image 35a taken with the electronic endoscope 11 having the CCD 24 in a correct mounting location and orientation (see FIG. 5A).

The processing device 12 calibrates the endoscope image 30 in accordance with the positional and rotational displacement amounts of the test chart image 35a obtained in the displacement measuring mode. Thereby, the endoscope image 30 with no positional and rotational displacements is obtained regardless of the mounting location and the orientation of the CCD 24. The positional and rotational displacement amounts of the test chart image 35a are measured in, for example, displacement inspection that is one of pre-shipment inspections of the electronic endoscope 11.

During the displacement measuring mode, the distal portion 16c is held in the endoscope alignment mechanism 14 in a position opposing the test chart 35. The endoscope alignment mechanism 14 is composed of a flat stage 14a on which the test chart 35 is placed, and a holder 14b for holding the distal portion 16c.

Figure 2:
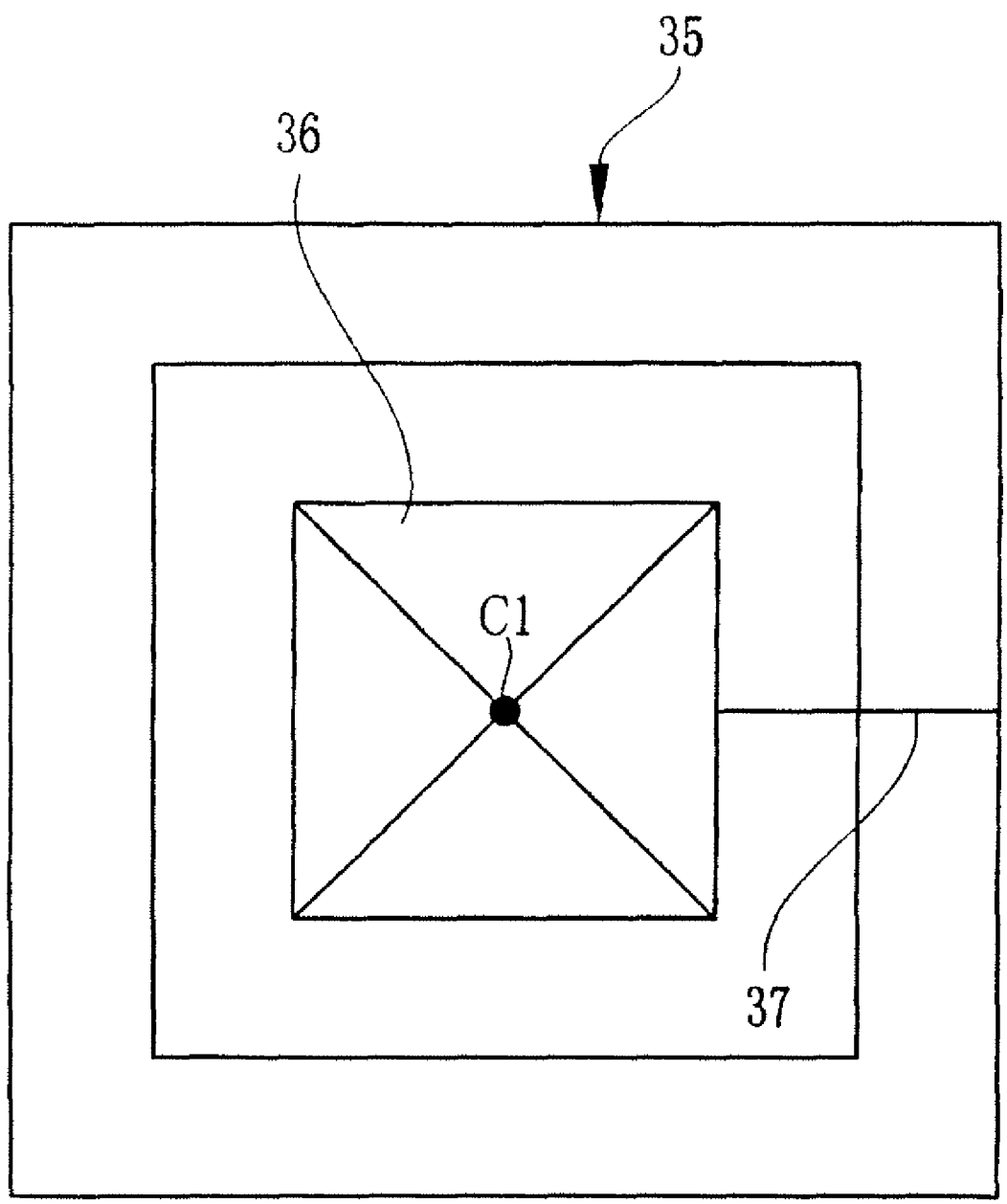
FIG. 2 is a plan view of a test chart.

In FIG. 2, the test chart 35 has a chart alignment mark 36 for showing a center C1 of the test chart 35, and an orientation detection mark 37 used for detecting the orientation of the test chart 35. The chart alignment mark 36 and the orientation detection mark 37 make up a test pattern of the present invention. It should be noted that a numeral 36a indicates the chart alignment mark, and a numeral 37a indicates the orientation detection mark in the test chart image 35a (see FIG. 5A). It should be noted that FIG. 2 is an example of the test chart. The test chart may be changed depending on, for example, the type of the electronic endoscope 11 used.

The chart alignment mark 36 is a square with its diagonal lines. The orientation detection mark 37 is a line positioned on the right side of the center C1 and parallel to a horizontal line passing the center C1. Orientation of the test chart image 35a displayed on a screen (hereinafter referred to as monitor screen) of the monitor 31 is detected by a tilt angle of the orientation detection mark 37a (see FIGS. 5A, 7, 10A, and 10B). With this orientation detection mark 37, rotational displacement of the test chart image 35a is detected, and a rotational displacement amount of the test chart image 35a is obtained.

Referring back to FIG. 1, the holder 14b is substantially L-shaped. The holder 14b extends vertically upward from the flat stage 14a, and a top portion thereof is curved by 90 degrees, positioned above the test chart 35. A setting hole 38 is formed through the top portion of the holder 14 in a position vertically above the chart alignment mark 36. The setting hole 38 is formed through the holder 14 such that the center of the CCD 24 with the correct mounting location and the center C1 of the test chart 35 coincide with each other when the distal portion 16c is inserted into the setting hole 38. It should be noted that silk screen printing or slight projections and depressions are formed on a circumference of the distal portion 16c. The distal portion 16c is held in the setting hole 38 by friction between the setting hole 38 and the silk screen printing or the projections and depressions. Thus, the distal portion 16c is positioned vertically above the chart alignment mark 36.

The setting hole 38 rotatably holds the distal portion 16c in a circumferential position. An inspector manually rotates the distal portion 16c in the circumferential direction to align the distal portion 16c with a proper circumferential position. To facilitate this alignment, the circumferential surface of the distal portion 16c and an outer edge portion of the setting hole 38 may be marked with alignment marks used for the alignment. A reference position and a reference orientation of the test chart image 35a is determined by aligning the distal portion 16c with the proper circumferential position with respect to the position of the setting hole 38.

In this embodiment, the position of the setting hole 38 and the proper circumferential position of the distal portion 16c are determined such that the reference position of the test chart image 35a satisfies the condition (1), and the reference orientation of the test chart image 35a satisfies the condition (2) as described below (see FIG. 5A).

(1) The center C1 of the chart alignment mark 36a of the test chart image 35a is positioned at the center of the monitor screen.

(2) The orientation detection mark 37a of the test chart image 35a is positioned on the right of the center C1, parallel to the horizontal direction of the monitor screen.

Figure 3:
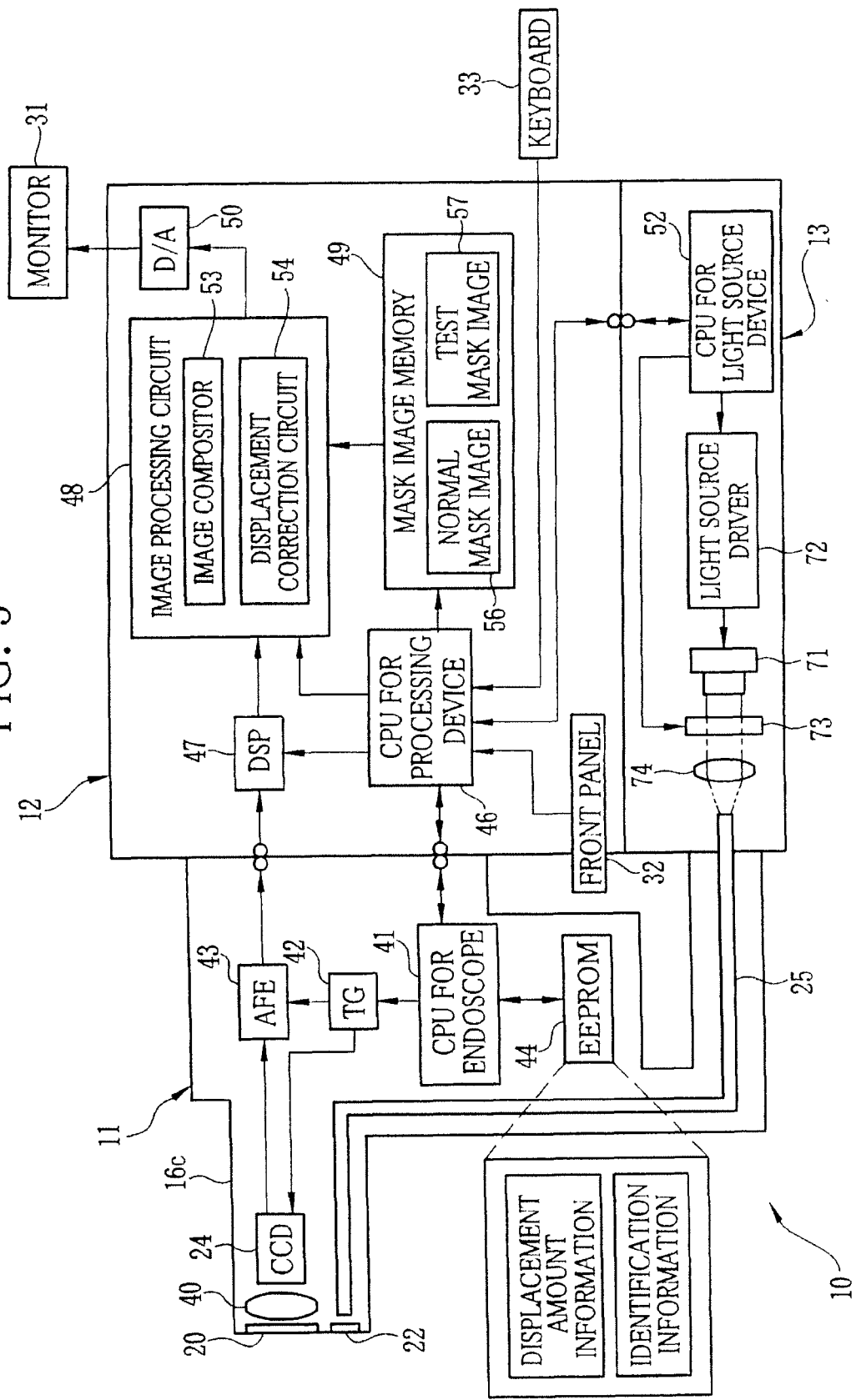
FIG. 3 is a block diagram showing electric configuration of the electronic endoscope system.

As shown in FIG. 3, the CCD 24 is incorporated in the distal portion 16c of the electronic endoscope 11. The CCD 24 is disposed at an image-forming position of an objective lens 40 provided in the rear of the image capturing window 20. The electronic endoscope 11 is also provided with a CPU 41, a timing generator (TG) 42, an analog front end (AFE) 43, an EEPROM (external memory device, memory) 44.

The CPU 41 for the electronic endoscope 11 carries out communications with the CPU 46 for the processing device 12 to control operation of each part of the electronic endoscope 11. The EEPROM 44 is connected to the CPU 41. The EEPROM 44 stores identification information for identifying the type of the electronic endoscope 11, and measurement results of positional and rotational displacement amounts of the test chart image 35a. Based on the information delivery request from the CPU 46, the CPU 41 reads the identification information or displacement amount information stored in the EEPROM 44 and sends the read information to the CPU 46.

The TG 42 generates drive pulses (vertical/horizontal scanning pulses, reset pulses, or the like) for the CCD 24, and synchronization pulses for the AFE 43 under the control of the CPU 41. The CCD 24 is driven by the drive pulses input from the TG 42. The CCD 24 photoelectrically converts an optical image formed with the objective lens 40 into image signals and outputs the image signals.

The AFE 43 is made up of a correlated double sampling (CDS) circuit, a programmable gain amplifier (PGA), and an A/D converter. The CDS circuit performs correlated double sampling to the image signals output from the CCD 24 to reduce reset noise and amplifier noise generated in the CCD 24. Then, the PGA amplifies the image signals with a predetermined amplification factor designated by the CPU 41.

Thereafter, the A/D converter converts the image signals into digital image signals of predetermined bits. The digital image signals output from the AFE 43 are input to the processing device 12 through the sub-connector 29b.

The processing device 12 includes a CPU 46, a digital signal processor (DSP) 47, an image processing circuit 48, a mask image memory 49, and a D/A converter 50. The CPU 46 controls every section of the processing device 12 and wholly controls the electronic endoscope system 10.

To the CPU 46 are connected the front panel 32, the keyboard 33, the CPU 41 for the electronic endoscope 11, the mask image memory 49. The CPU 46 switches the operation mode of the processing device 12 between the normal mode and the displacement measuring mode in accordance with the operation mode selected on the front panel 32.

Controlled by the CPU 46, the DSP 47 carries out color interpolation, color separation, color balance adjustment, gamma correction, image enhancement and the like to the image signals of one frame input from the AFE 43 of the electronic endoscope 11 to generate the endoscope image 30. Then, the DSP 47 outputs the endoscope image 30 to the image processing circuit 48.

The image processing circuit 48 includes an image compositor 53 and a displacement correction circuit 54. The image compositor 53 overlays a mask image stored in the mask image memory 49 on the endoscope image 30 input from the DSP 47. In the mask image memory 49, the normal mask images 56 and test mask images 57 are stored.

Under the control of the CPU 46, the image compositor 53 overlays the normal mask image 56 on the endoscope image 30 when the processing device 12 is in the normal mode. The endoscope image 30 has already been subjected to the displacement correction (calibration) by the displacement correction circuit 54, which will be described later.

As shown in FIG. 4A, the endoscope image 30 is an observation image 58 of the body cavity edged with a lens barrel frame (not shown) retaining the objective lens 40. The observation image 58 is surrounded by a substantially circular uneven portion 59 because of the lens barrel frame. The uneven portion 59A is surrounded by a blank area 60. The blank area 60 is caused by vignetting. As shown in FIG. 4B, the normal mask image 56 has an unmasked area 61 that exposes a center portion of the endoscope image 30. The unmasked area 61 is an area inside an inscribed circle of the uneven portion 59, and the normal mask image 56 covers the uneven portion 59 when the normal mask image 56 is overlaid on the endoscope image 30. The image compositor 53 composites the normal mask image 56 and the endoscope image 30 such that the normal mask image 56 is overlaid on the endoscope image 30 to generate a normal mask composite image 62 as shown in FIG. 4C.

Since positions and sizes of the uneven portion 59 in the endoscope image 30 differ depending on the type of the electronic endoscope 11, a plurality of normal mask images 56 and the test mask images 57 with the unmasked areas different in size and shape are stored in the mask image memory 49. The CPU 46 selects a mask image suitable for the endoscope image 30 from the mask image memory 49 based on the identification information of the electronic endoscope 11 input from the CPU 41, and supplies the selected mask image to the image compositor 53.

Referring back to FIG. 3, the image compositor 53 outputs the normal mask composite image 62 to the D/A converter 50. The D/A converter 50 converts the normal mask composite image 62 into analog signals and outputs them to the monitor 31.

Under the control of the CPU 46, when the processing device 12 is in the displacement measuring mode, the image compositor 53 composites the test mask image (reference image) 57 and an endoscope image 30a obtained by taking an image of the test chart 35.

As shown in FIG. 5A, the endoscope image 30a is the same as the endoscope image 30 except that an observation image 63 containing the test chart image 35a is displayed on the monitor screen instead of the observation image 58. As shown in FIG. 5B, the test mask image 57 has an unmasked area 64 and a reference pattern. The unmasked area 64 is the same as the unmasked area 61 and exposes only the center portion of the endoscope image 30a. A reference pattern 65 with the crossed lines indicates a reference position and a reference orientation of the test chart image 35a.

The reference pattern 65 has a horizontal line 65a and a vertical line 65b. The horizontal line 65a passes the center C2 of the test mask image 57, and is parallel to the horizontal direction of the monitor screen. The vertical line 65b passes the center C2 of the test mask image 57, and is orthogonal to the horizontal line 65a. An intersection point of the horizontal line 65a and the vertical line 65b indicates the center C2 of the test mask image 57. The center C2 coincides with the center of the monitor screen. Thus, the center C2 of the test mask image 57 becomes a reference position mark indicating a reference position of the test chart image 35a.

The horizontal line 65a of the reference pattern 65 is parallel to horizontal direction of the monitor screen. When a rotational displacement amount of the test chart image 35a is zero, the orientation detection mark 37a becomes parallel to the horizontal line 65a. When both the positional displacement amount and the rotational displacement amount of the test chart image 35a are zero, the orientation detection mark 37a overlaps with the horizontal line 65a. Thus, the horizontal line 65a becomes a reference orientation mark indicating a reference orientation of the test chart image 35a.

As shown in FIG. 5C, the image compositor 53 composites the test mask image 57 and the endoscope image 30a such that the test mask image 57 is overlaid on the endoscope image 30a to generate a test mask composite image 67. The test mask composite image 67 is converted into analog signals in the D/A converter 50 and displayed on the monitor 31.

In an ideal state in which the test chart image 35a is displayed in a reference position and a reference orientation, the center C1 of the test chart image 35a coincides with the center C2 of the test mask image 57. The orientation detection mark 37a of the test chart image 35a overlaps with the horizontal line 65a.

On the other hand, when the test chart image 35a is displaced from the reference position, the center C1 thereof does not coincide with the center C2 of the test mask image 57. In this case, the positional displacement amount of the test chart image 35a is a positional displacement amount of the center C1 (chart alignment mark 36a) with respect to the center C2 (the intersection point of the horizontal and vertical lines 65a and 65b). In other words, the positional displacement amount is a distance between the chart alignment mark 36a and the reference position mark. This positional displacement amount is represented by a positional displacement amount in a horizontal direction (horizontal displacement amount) and a positional displacement amount in a vertical direction (vertical displacement amount).

When the test chart image 35a is rotationally displaced with respect to the reference position, the orientation detection mark 37a is tilted with respect to the horizontal line 65a. A rotational displacement amount of the test chart image 35a is represented by a tilt angle between the orientation detection mark 37a and the horizontal line (hereinafter may referred to as X-axis) 65a (see FIG. 7).

The unmasked area 64 of the test mask image 57 is provided with scale lines 68 for obtaining position coordinates of the center C1 of a test chart image 65a and the orientation detection mark 37a. In the scale lines 68, the X-axis is the horizontal line 65a, the Y-axis is the vertical line 65b, and the origin is the center C2 of the test mask image 57. The positional and rotational displacement amounts are obtained by measuring the position coordinates of the center C1 and the orientation detection mark 37a of the test chart image 35a based on the scale lines 68. It should be noted that the scale lines 68 are evenly spaced. Each square formed by the scale lines 68 contains N×N pixels (N: natural number).

Next, specific steps for obtaining the positional and rotational displacement amounts of the test chart image 35a are described. In this embodiment, an inspector visually measures the position coordinates of the center C1 and the orientation detection mark 37a of the test chart image 35a in the scale lines 68 in the test mask image 57 and obtains the positional and rotational displacement amounts based on the measurement. First, the test chart image 35a only with the positional displacement is described.

Figure 6:
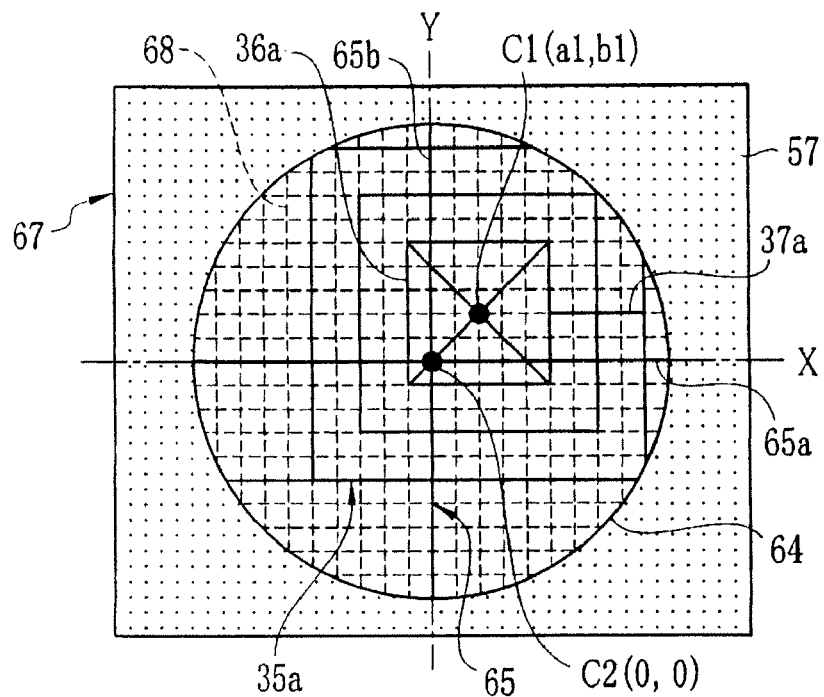
FIG. 6 is an explanatory view illustrating measurement of a positional displacement amount of the test chart image only with the positional displacement.

As shown in FIG. 6, the origin of the scale lines 68 is the center C2 of the test mask image 57. The position coordinates (X, Y) of the center C2 are expressed as (X, Y)=(0, 0). The inspector visually measures the position coordinates (X,Y) of the center C1 of the test chart image 35a, expressed as (X, Y)=(a1, b1). When the center C1 is inside a square of the scale lines 68, each of the position coordinates are visually estimated to one or two digits to the right of the decimal. The "a1" represents the horizontal displacement amount (X-coordinate) and the "b1" represents the vertical displacement amount (Y-coordinate). In this example, (a1, b1)=(2, 2). In a case that the CCD 24 has a large number of pixels, an area close to the test chart image 35a including the chart alignment mark 36a may be enlarged to distinguish the center C1 easily.

Next, the inspector converts the horizontal displacement amount a1 represented by the X-coordinate and the vertical displacement amount b1 represented by the Y-coordinate into a horizontal displacement amount A and a vertical displacement amount B each represented by the number of pixels. A relation between the scale line 68 and the number of pixels is well known, for example, one coordinate=N pixels. This relation is invariant in the same CCD. Therefore, values "A" and "B" are calculated by multiplying N to each of the values "a1" and "b1". Thus, the positional displacement amount (the horizontal displacement amount A and the vertical displacement amount B) of the test chart image 35a is obtained.

Figure 7:
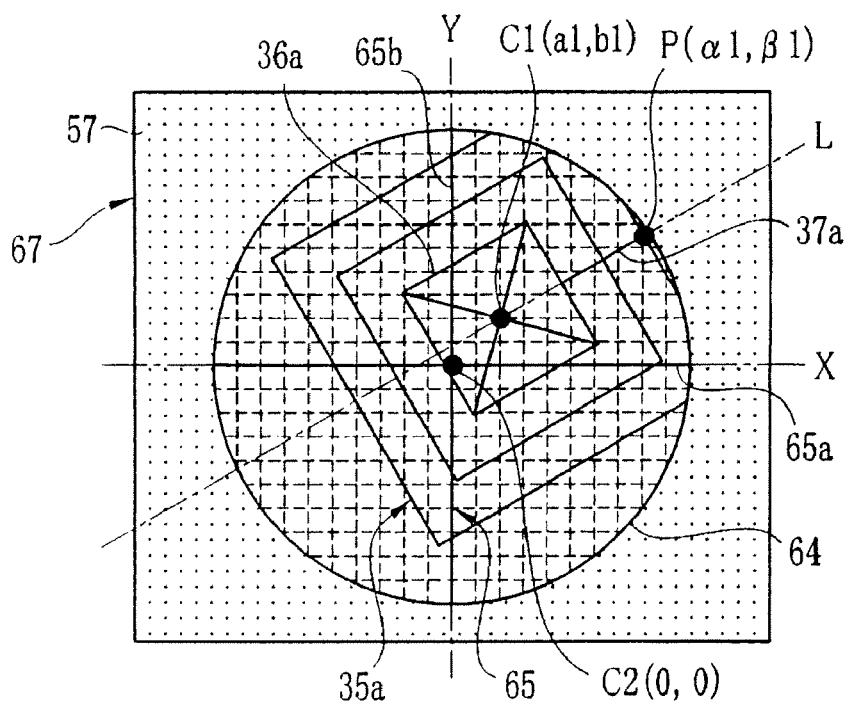
FIG. 7 is an explanatory view illustrating measurement of positional and rotational displacement amounts of the test chart with both the positional and rotational displacements.

As shown in FIG. 7, when the test chart image 35a is both positionally and rotationally displaced, the inspector visually measures the position coordinates of the center C1 of the test chart image 35a and position coordinates of a given point P on the orientation detection mark 37a using the scale lines 68. It should be noted that the horizontal line 65a is the X-axis in this embodiment. Therefore, the rotational displacement amount is obtained without obtaining the position coordinates of the horizontal line 65a.

In this embodiment, the position coordinates (X, Y) of the center C1 are the same as in the FIG. 6, (X, Y)=(a1, b1). The position coordinates (X,Y) of the point P are expressed as (X, Y)=(α1, β1).

The inspector calculates the positional displacement of the center C1 of the test chart image 35a. Then, the inspector obtains the rotational displacement amount of the test chart image 35a, that is, a tilt angle θ of the orientation detection mark 37a with respect to the horizontal line 65a of the reference pattern 65. Since the horizontal line 65a is the X axis (second line), the tilt angle θ of the orientation detection mark 37a is a tilt angle θ between the X axis and a line L (first line) passing the center C1 and the point P. The tilt angle θ is calculated using the mathematical expression (1) below.

$$\text{tilt angle } \theta = \tan^{-1}\{(|1-b1|)/(\alpha1-a1)\} \quad (1)$$

Thus, the rotational displacement amount (tilt angle θ) is obtained. If the test chart image 35a is only rotationally displaced, both the centers C1 and C2 have the position coordinates (X,Y) of (X,Y)=(0, 0). The tilt angle θ is calculated by substituting 0 into a1 and b1 in the above mathematical expression (1).

Referring back to FIG. 3, the keyboard 33 is used for inputting the horizontal displacement amount A, the vertical displacement amount B, and the tilt angle θ obtained by the inspector. When the processing device 12 is in the displacement measuring mode, a displacement amount entry screen (not shown) is displayed together with the test mask composite image 67 on the monitor screen. The inspector inputs the horizontal and vertical displacement amounts A, B, and the tilt angle θ using the keyboard 33 according to the instructions displayed on the displacement amount entry screen.

The CPU 46 for the processing device 12 outputs the horizontal and vertical displacement amounts A, B and the tilt angle θ as displacement amount information to the CPU 41 for the electronic endoscope 11. The CPU 41 stores the displacement amount in the EEPROM 44.

The CPU 46 issues a delivery request for the displacement amount information to the CPU 41 when the processing device 12 is switched to the normal mode. In response to this, the displacement amount information is input to the CPU 46 from the CPU 41. The CPU 46 outputs the displacement amount information to the displacement correction circuit 54.

In the normal mode, the displacement correction circuit 54 calibrates the endoscope image 30 input from the DSP 47 based on the displacement amount information (the horizontal and vertical displacement amounts A and B, and the tilt angle θ) input from the CPU 46. Thus, the positional and rotational displacement amounts of the endoscope image 30 are corrected as shown in FIG. 5C. A technique to calibrate is well-known, for example, a general-purpose graphics LSI for display control with positional displacement and rotation functions may be used. Accordingly, the description thereof is omitted. The displacement correction circuit 54 outputs the corrected endoscope image 30 to the image compositor 53.

The light source device 13 is composed of a CPU 52, a light source 71, a light source driver 72, an aperture mechanism 73, and a condenser lens 74. The CPU 52 carries out communications with the CPU 46, and controls the light source driver 72 and the aperture mechanism 73. The light source 71 may be a xenon lamp or a halogen lamp, and controlled by the light source driver 72. The aperture mechanism 73 is disposed on the light emission side of the light source 71, and increases or decreases a light amount incident on the condenser lens 74. The condenser lens 74 condenses the light that passed the aperture mechanism 73 and guides it to a light inlet of the light guide 25 of the electronic endoscope 11 connected to the light source device 13. The light guide 25 is inserted from the base of the electronic endoscope 11 to the distal portion 16c. A light outlet of the light guide 25 is connected to the lighting window 22.

Figure 8:
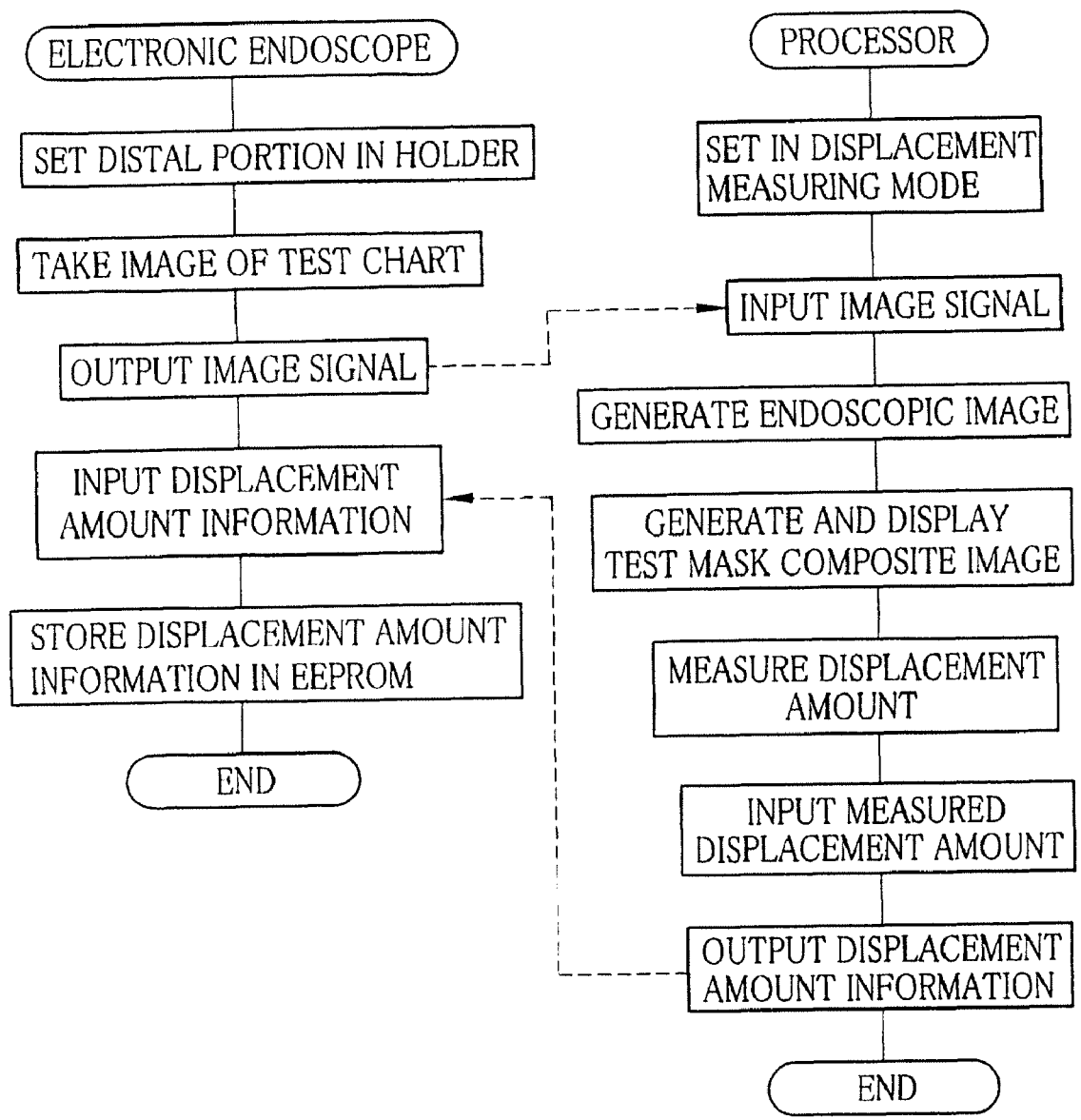
FIG. 8 is a flowchart illustrating steps for displacement inspection.
Figure 9:
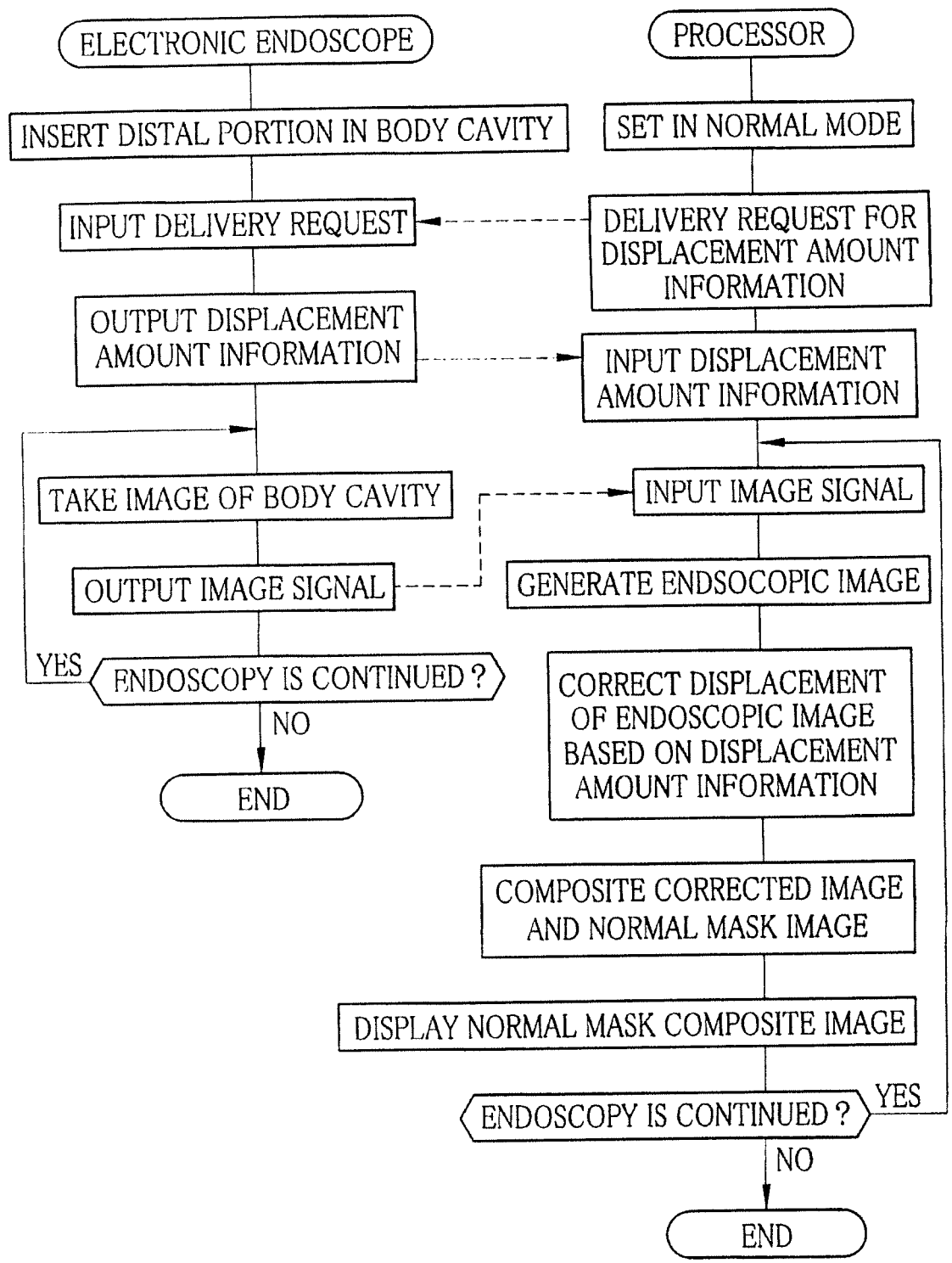
FIG. 9 is a flowchart illustrating steps for displacement correction performed by the processing device.

Next, referring to flowcharts in FIGS. 8 and 9, steps for the displacement inspection of the electronic endoscope 11 and the calibrating steps for the displacement correction performed by the processing device 12 are described. In FIG. 8, the inspector sets the distal portion 16c of the electronic endoscope 11 in the setting hole 38 of the holder 14b as preparation to the displacement inspection. Then, the inspector manually rotates the distal portion 16c in a circumferential direction to align the distal portion 16c with the proper circumferential position.

The inspector connects the electronic endoscope 11 to the processing device 12 and the light source device 13 and turns on the processing device 12 and the light source device 13 in this order. If the inspection room is well lit, the light source device 13 is unnecessary. Then, the inspector operates the switches on the front panel 32 of the processing device 12 to set the processing device 12 in the displacement measuring mode. An image of the test chart 35 is taken with the CCD 24 of the electronic endoscope 11 while the test chart 35 is illuminated by illumination light from the light source device 13. The image signals output from the CCD 24 are converted into digital signals in the AFE 43. Thereafter, the image signals are input to the processing device 12.

In the processing device 12, the DSP 47 generates the endoscope image 30a from the image signals of one frame input from the AFE 43 of the electronic endoscope 11. The generated endoscope image 30a is input to the image processing circuit 48. The CPU 46 for the processing device 12 selects from the mask image memory 49 a test mask image 57 suitable for the endoscope image 30a based on the endoscope identification information input from the CPU 41 for the electronic endoscope 11, and supplies the selected test mask image 57 to the image compositor 53. It should be noted that in the displacement measuring mode, the displacement correction circuit 54 stops.

The image compositor 53 composites the test mask image 57 and the endoscope image 30a to generate the test mask composite image 67, and outputs this test mask composite image 67 to the D/A converter 50. The test mask composite image 67 is converted into analog signals by the D/A converter, and displayed on the monitor screen.

The inspector measures the position coordinates of the center C1 of the test chart image 35a and the point P on the orientation detection mark 37a with the use of the scale lines 68 in the test mask composite image 67 as described with reference to FIGS. 6 and 7. The inspector calculates the positional displacement amount (horizontal and vertical displacement amounts A and B) of the test chart image 35a based on the measured position coordinates of the center C1. The inspector calculates the rotational displacement amount (the tilt angle θ of the orientation detection mark 37a) of the test chart image 35a by substituting the position coordinates of the center C1 and the point P into the above mathematical expression (1).

Thereafter, the inspector inputs the horizontal displacement amount A, the vertical displacement amount B, and the tilt angle θ using the keyboard 33. The CPU 46 for the processing device 12 outputs the displacement amount information (the horizontal displacement amount A, the vertical displacement amount B, and the tilt angle θ) to the CPU 41 for the electronic endoscope 11. The displacement amount information is stored in the EEPROM 44 of the electronic endoscope 11. Thus, the displacement inspection is completed. Thereafter, the electronic endoscopes 11 are delivered to a hospital from a factory.

As shown in FIG. 9, in the hospital, to perform endoscopy of a body cavity using the electronic endoscope 11, the electronic endoscope 11 is connected to the processing device 12, and the processing device 12 is set in the normal mode. In the normal mode, the CPU 46 issues the delivery request for the displacement amount information to the CPU 41.

In response to the delivery request, the CPU 41 reads displacement amount information from the EEPROM 44 and outputs it to the CPU 46. The CPU 46 outputs the displacement amount information to the displacement correction circuit 54. At the same time, the CPU 46 selects the normal mask image 56 from the mask image memory 49 based on the identification information of the electronic endoscope 11 input from the CPU 41, and supplies the normal mask image 56 to the image compositor 53.

After the processing device 12 is set in the normal mode, the insert section 16 of the electronic endoscope 11 is inserted in the body cavity of a patient. An image of the body cavity is taken with the CCD 24 while the body cavity is illuminated with the illumination light from the light source device 13. Image signals obtained by the CCD 24 are input to the processing device 12. The DSP 47 generates the endoscope image 30 and inputs this endoscope image 30 to the image processing circuit 48.

In the image processing circuit 48, the displacement correction circuit 54 calibrates the endoscope image 30 based on the displacement amount information. Thus, the positional and rotational displacements of the endoscope image 30 are corrected. Thereafter, the displacement correction circuit 54 outputs the corrected endoscope image 30 to the image compositor 53.

The image compositor 53 composites the normal mask image 56 and the corrected endoscope image 30 and generates the normal mask composite image 62. The normal mask composite image 62 is output to the D/A converter 50. In the D/A converter 50, the normal mask composite image 62 is converted into the analog signals, and then displayed on the monitor screen. Until the end of the endoscopy, the image signals are input to the processing device 12 from the electronic endoscope 11, and the displacement of the endoscope image 30 is corrected in the processing device 12, and the normal mask composite image 62 is displayed on the monitor screen, sequentially.

As described above, in the electronic endoscope system 10 of the present invention, the positional and rotational displacement amounts of the test chart image 35a with respect to the reference pattern 65 is calculated, and the displacement of the endoscope image 30 is corrected based on the calculation results. As a result, the positional and rotational displacements of the endoscope image 30 are corrected without providing a mechanical structure for correcting the position and the orientation of the CCD 24. In other words, the endoscope image 30 with no positional and rotational displacements is obtained regardless of mounting location accuracy of the CCD 24. Thus, the endoscope image 30 with no positional and rotational displacements is obtained without the use of the mechanical structure even if the number of the pixels of the CCD 24 is further increased.

The production cost is reduced by not requiring the additional mechanical structure. In addition, the mounting location accuracy of the CCD 24 is relaxed. This also relaxes processing accuracy of parts used for attaching and positioning the CCD 24. As a result, the production costs of such parts are reduced. Relaxing the mounting location accuracy of the CCD 24 also makes the attachment of the CCD 24 easy and improves production yield of the electronic endoscope 11.

Next, a second embodiment of the present invention is described. In the displacement inspection of the first embodiment, with the use of the test mask composite image 67 displayed on the monitor screen, the positional and rotational displacement amounts of the test chart image 35a are obtained at a time. In the displacement inspection of the second embodiment, on the other hand, the measurement and the correction of the positional displacement amount are performed prior to those of the rotational displacement amount. Hereinafter, with reference to FIGS. 10A, 10B and 11, the displacement inspection of the second embodiment is detailed. It should be noted that the devices shown in FIGS. 1 to 3 are used in the second embodiment in the same manner as in the first embodiment.

Figure 10A:
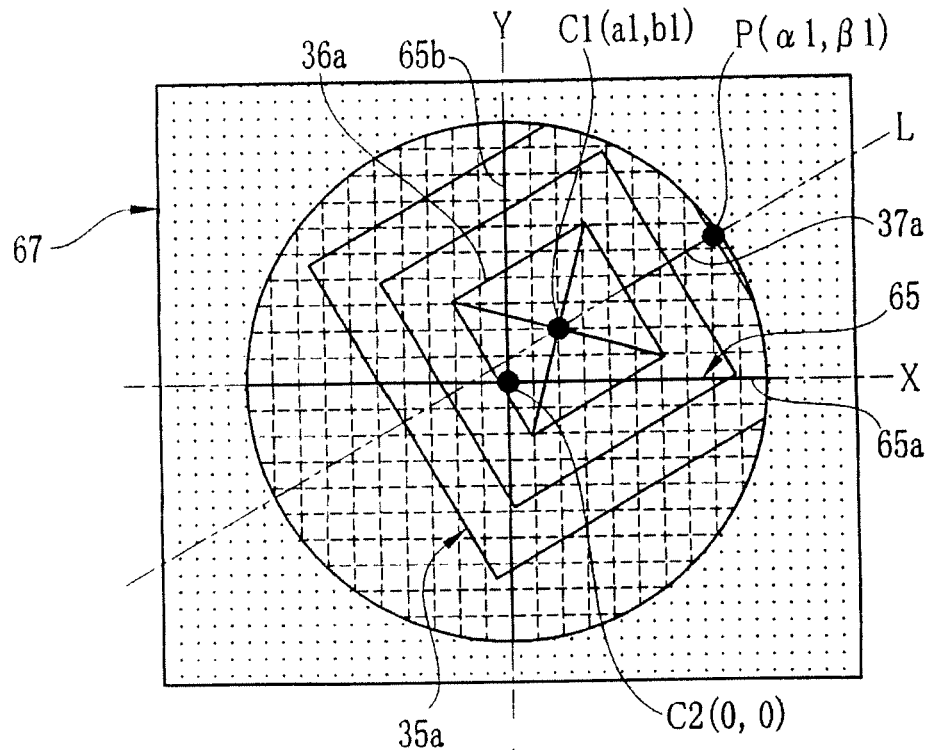
FIGS. 10A and 10B are explanatory views illustrating the measurement of the rotational displacement amount performed after the positional displacement amount is measured and corrected.
Figure 11:
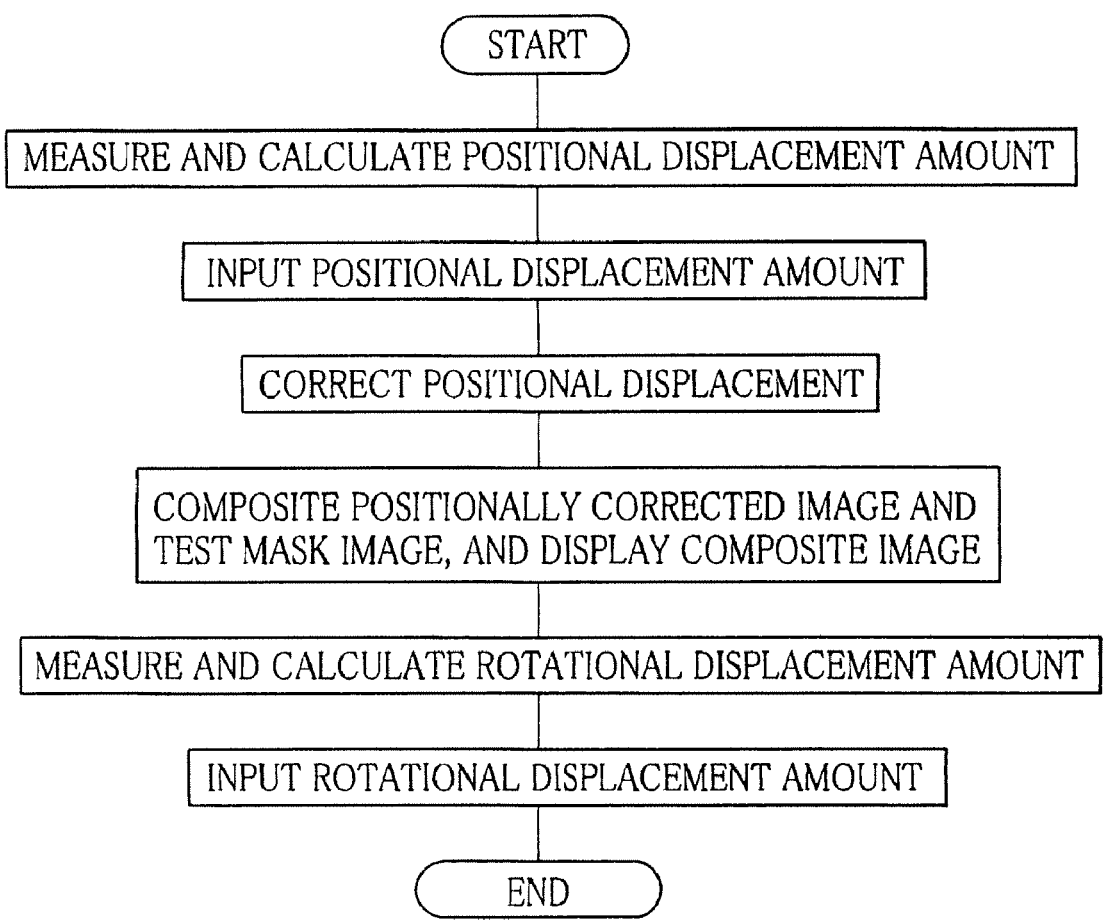
FIG. 11 is an explanatory view illustrating steps for the displacement inspection in which the positional displacement amount is measured and corrected first.

As shown in FIGS. 10A and 11, the inspector visually measures the position coordinates (X, Y)=(a1, b1) of the center C1 of the test chart image 35a. Based on this measurement, the positional displacement amount (the horizontal displacement amount A and the vertical displacement amount B) of the test chart image 35a is calculated. Then, the inspector inputs the horizontal displacement amount A and the vertical displacement amount B using the keyboard 33. The CPU 46 for the processing device 12 outputs the positional displacement information containing the horizontal displacement amount A and the vertical displacement amount B to the CPU 41 for the electronic endoscope 11 and the displacement correction circuit 54.

The displacement correction circuit 54 actuates in response to the input of the positional displacement information from the CPU 46. Based on this positional displacement information, the displacement correction circuit 54 performs positional displacement correction to the endoscope image 30a output from the DSP 47 so that the center C1 of the test chart image 35a coincides with the center C2 of the test mask image 57. Then, the displacement correction circuit 54 outputs the corrected endoscope image 30a to the image compositor 53.

Figure 10B:
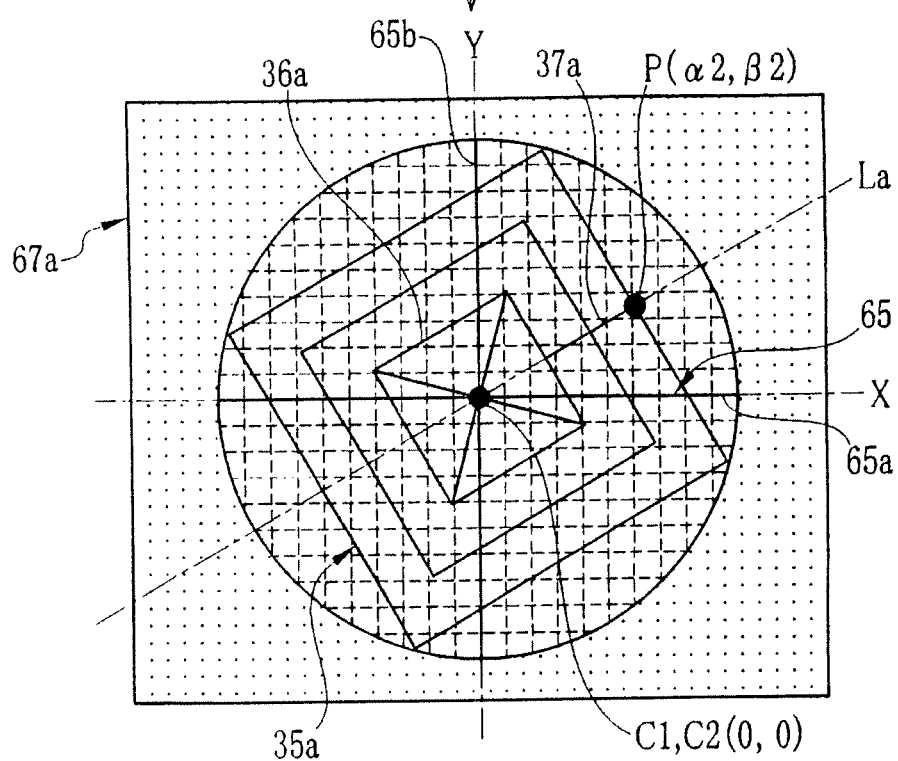

The image compositor 53 composites the test mask image 57 and the corrected endoscope image 30a and generates a test mask composite image 67a (see FIG. 10B). Then, the image compositor 53 outputs the test mask composite image 67a to the D/A converter 50. Thereby, the test mask composite image 67a is displayed on the monitor screen.

As shown in FIG. 10B, with the use of the scale lines 68, the inspector visually measures the position coordinates of the point P on the orientation detection mark 37a. The position coordinates (X, Y) of the point P is (X, Y)=(α2, β2). In a case that the position coordinates (X, Y) of the point P before the positional displacement correction is (X, Y)=(α1, β1), α2 and β2 are obtained by the following mathematical expressions: α2=α1–a1, β2=β1–b1. The tilt angle θ of the orientation detection mark 37a is, in this case, a tilt angle between a line La, passing the origin and the point P, and the X-axis (the horizontal line 65a). The tilt angle θ is obtained by substituting the position coordinates of the point P in the mathematical expression (2) below.

$$\text{tilt angle } \theta=\tan^{-1}(\beta 2/\alpha 2) \quad (2)$$

Next, the tilt angle θ is input through the keyboard 33. Thereby, all of the displacement amount information (the horizontal displacement amount A, the vertical displacement amount B, and the tilt angle θ) is input and stored in the EEPROM 44 of the electronic endoscope 11. The displacement inspection is thus completed. The processing from then on is the same as that in the first embodiment, and the description thereof is omitted.

As described above, in the displacement inspection of the second embodiment, the measurement of the positional displacement amount and the positional displacement correction are performed first. Accordingly, the tilt angle θ (the rotational displacement amount) of the orientation detection mark 37a is calculated using the mathematical expression (2) that is easier than the mathematical expression (1) of the first embodiment. Thus, the tilt angle θ is calculated easily.

Next, a third embodiment of the present invention is described. In the first and the second embodiments, the inspector measures and calculates the positional and rotational displacement amounts and inputs the measurement results to the processing device 12. In an electronic endoscope system 80 of the third embodiment, on the other hand, a processing device 81 measures the positional and rotational displacement amounts (see FIG. 12).

Figure 12:
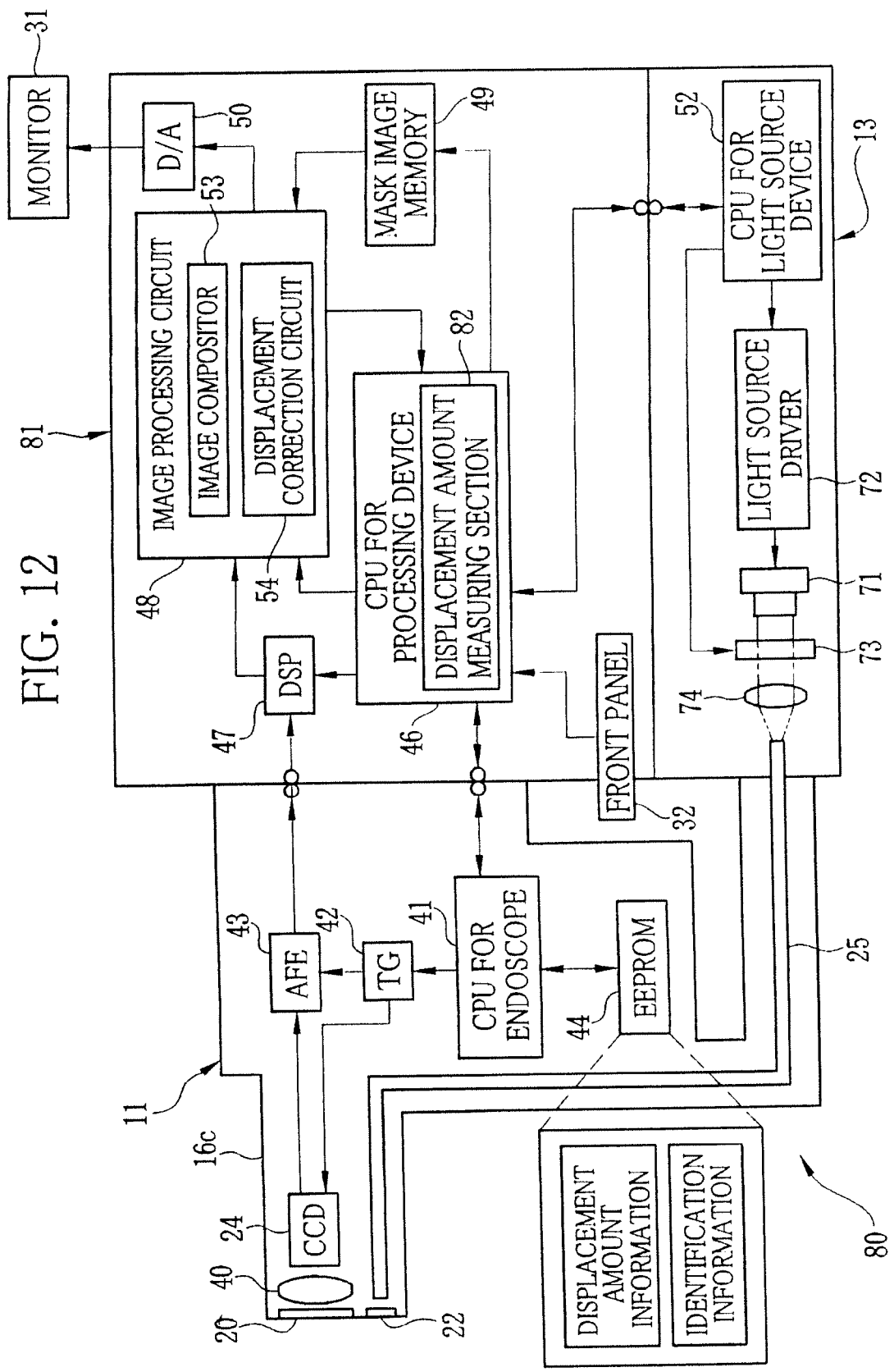
FIG. 12 is a schematic view of an electronic endoscope system of another embodiment in which a processing device measures the positional and rotational displacement amounts.

In FIG. 12, the CPU 46 controls the processing device 81 and functions as a displacement amount measuring section 82 for measuring the positional and rotational displacement amounts. In the displacement measuring mode, under the control of the CPU 46, the image compositor 53 outputs the test mask composite image 67 shown in FIG. 6 or FIG. 7 to the CPU 46.

The displacement amount measuring section 82 performs image analysis to the test mask composite image 67 input from the image compositor 53, and detects the intersection point of the horizontal line 65a and the vertical line 65b as the center C2 of the test mask image 57, and the center C1 of the chart alignment mark 36a.

Next, the displacement amount measuring section 82 measures the numbers of pixels by which the center C1 is displaced from the center C2 as the origin in the horizontal and vertical directions of the screen. Thereby, the horizontal displacement amount A and the vertical displacement amount B are obtained as in the first and second embodiments. A technique to detect the center positions C1 (the chart alignment mark 36a) and C2 (the intersection point of the horizontal line 65a and the vertical line 65b) by image analysis of the test mask composite image 67 and a technique to measure the number of pixels between the centers C1 and C2 in the horizontal and vertical directions are well-known and descriptions thereof are omitted.

The displacement amount measuring section 82 performs image analysis to the test mask composite image 67 and detects the position of the point P on the orientation detection mark 37a and measures the numbers of pixels by which the point P is displaced from the center C2 in the horizontal and vertical directions. Thereby, a horizontal displacement amount Ap and a vertical displacement amount Bp of the point P are obtained. Then, the displacement amount measuring section 82 calculates the tilt angle θ of the orientation detection mark 37a using the mathematical expression (3) below in which the positional displacement amounts A, B, Ap and Bp substitute for the parameters a1, b1, α1 and β1 of the mathematical expression (1), respectively.

$$\text{tilt angle } \theta=\tan^{-1}\{(Bp-B)/(Ap-A)\} \quad (3)$$

Thus, the measurement of the horizontal displacement amount A, the vertical displacement amount B, and the tilt angle θ by the displacement amount measuring section 82 is completed. The CPU 46 for the processing device 81 outputs the displacement amount information obtained by the displacement amount measuring section 82 to the CPU 41 for the electronic endoscope 11. The processing from then on is the same as that in the first embodiment, and the description thereof is omitted.

In the third embodiment, the processing device 81 automatically measures the positional displacement amount and the rotational displacement amount during the displacement inspection. Therefore, burdens on the inspector are reduced and the displacement inspection is completed in a short time. It should be noted that the measurement and the correction of the positional displacement amount may be performed prior to the measurement and the correction of the rotational displacement amount as described in the second embodiment.

In the third embodiment, through the image analysis, the numbers of pixels by which the center C1 and the point P are displaced from the center (the origin) C2 in the horizontal and vertical directions of the screen are automatically measured. Therefore, it is unnecessary to provide the scale lines 68, allowing the use of the test chart and the test mask image different from the test chart 35 in FIG. 2 and the test mask image 5B in the first embodiment.

Figure 13A:
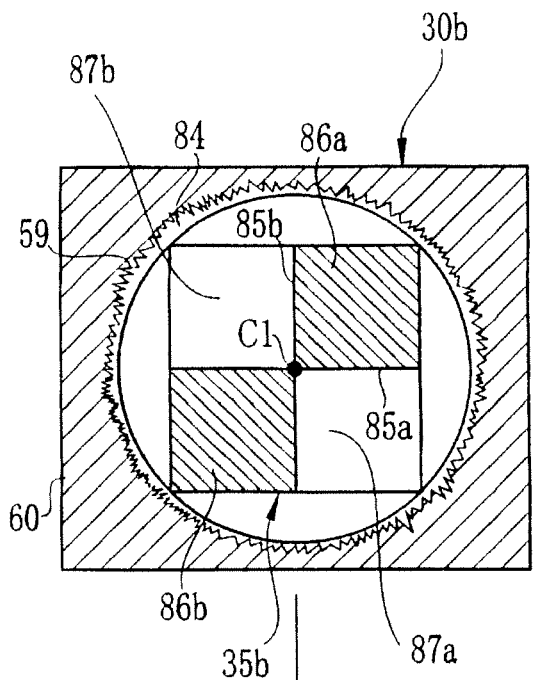
FIG. 13A is an explanatory view of a test chart image of another embodiment.

For example, as shown in FIG. 13A, an endoscope image 30b displays an observation image 84 containing a test chart image 35b. The test chart image 35b has a black and white checkered pattern. The test chart image 35b is quartered by a horizontal axis 85a and a vertical axis 85b both passing the center C1 (the chart alignment mark). Diagonally shaded quarter blocks 86a and 86b of the test chart image 35b are black. The other quarter blocks 87a and 87b are white.

Figure 13B:
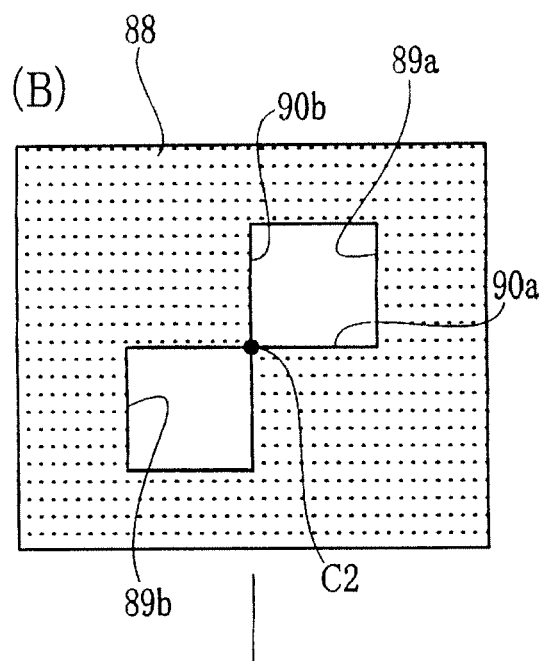
FIG. 13B is an explanatory view of a test mask image of another embodiment.

As shown in FIG. 13B, a test mask image 88 has unmasked areas 89a and 89b that coincide with the quarter blocks 86a and 86b when the displacement amount of the test chart image 35b is zero. The intersection point of the unmasked areas 89a and 89b coincides with the center C2 of the test mask image 88. The unmasked areas 89a and 89b serve as a reference pattern indicating a reference position and a reference orientation for the test chart image 35b. A numeral 90a is a horizontal edge of the unmasked areas 89a and 89b. A numeral 90b is a vertical edge of the unmasked areas 89a and 89b. The numerals 90a and 90b correspond to the horizontal line 65a and the vertical line 65b of the reference pattern 65 shown in FIG. 5B, respectively.

The image compositor 53 composites the endoscope image 30b and the test mask image 88 such that the test mask image 88 is overlaid on the endoscope image 30b to generate a test mask composite image 92.

Figure 13C:
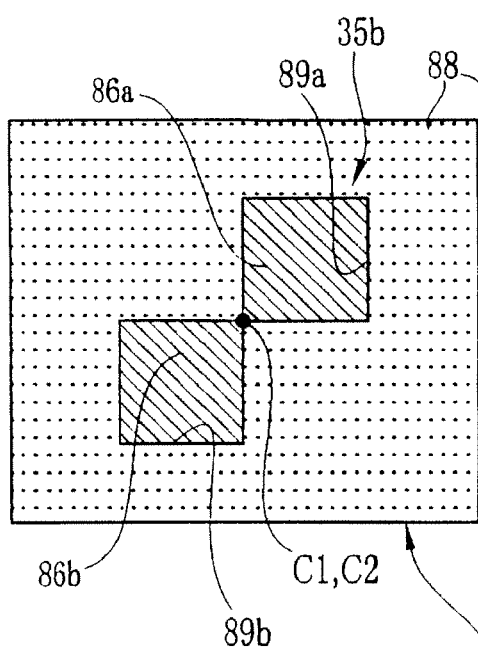
FIG. 13C is an explanatory view of a test mask composite image of another embodiment with no positional and rotational displacements.

As shown in FIG. 13C, in an ideal state in which the test chart image 35b is in the reference position and the reference orientation, the quarter block 86a is exposed through the unmasked area 89a, and the quarter block 86b is exposed through the unmasked area 89b. As a result, the test mask composite image 92 is entirely black.

Figure 13D:
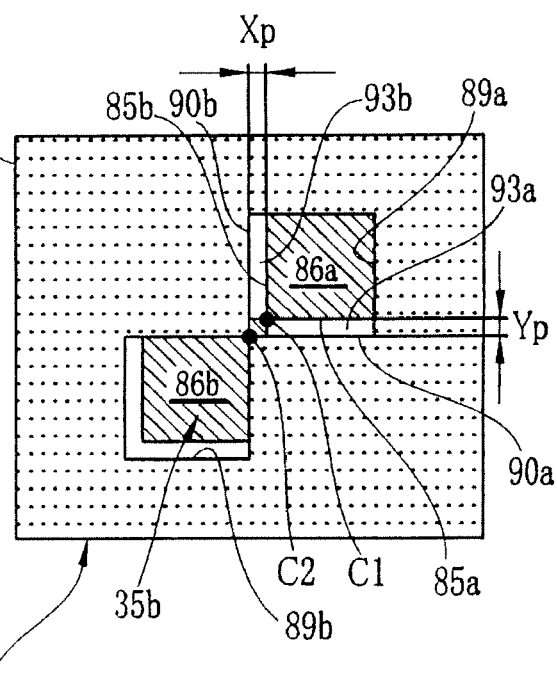
FIG. 13D is an explanatory view of a test mask composite image of another embodiment with the positional and rotational displacements.

On the other hand, as shown in FIG. 13D, when the test chart image 35b is displaced in the upper right direction from the reference position, for example, a strip of a white area 93a (a part of the white quarter block 87a) appears between the horizontal edge 90a of the unmasked area 89a and the horizontal axis 85a of the quarter block 86a. Also, a strip of a white area 93b (a part of the white quarter block 87a) appears between the vertical edge 90b and the vertical axis 85b.

The white area 93a shows a positional displacement of the test chart image 35b in the vertical direction, and is obtained by counting the number of pixels in a width Yp in the vertical direction of the white area 93a. The white area 93b shows positional displacement of the test chart image 35b in the horizontal direction, and is obtained by counting the number of pixels in a width Xp in the horizontal direction of the white area 93b. The counting of the numbers of pixels in the widths XP and YP is performed through the image analysis of the test mask composite image 92 by the displacement amount measuring section 82 as described in the third embodiment.

When the test chart image 35b is positionally displaced, for example, toward the lower right direction, the upper left direction, the lower left direction, the upper direction, or the like, from the reference position, only the positions and the number of the white areas change, and therefore the descriptions thereof are omitted. The image analysis is not necessarily required. When the test mask composite image 92 is displayed, the white areas 93a and 93b may be displayed at higher magnification, for example, and the inspector may count the numbers of pixels in the width Xp and the width Yp. In this case, the scale lines 68 are provided in the test mask image 88.

In a case that the test chart image 35a is rotationally displaced (not shown) from the reference position, the rotational displacement amount is represented by a tilt angle between the horizontal axis 85a and the horizontal edge 90a, or between the vertical axis 85b and the vertical edge 90b. In this case, the horizontal axis 85a and the vertical axis 85b are used as the orientation detection mark 37a described in the first embodiment. A method for obtaining the tilt angle between the horizontal axis 85a and the horizontal edge 90a is the same as the method for obtaining the tilt angle θ of the orientation detection mark 37 described in the first embodiment. A method for obtaining the tilt angle between the vertical axis 85b and the vertical edge 90b is also basically the same as that for obtaining the tilt angle θ of the orientation detection mark 37. Therefore, the description thereof is omitted. It is preferred that one of the quarter blocks 86a, 86b, 87a, and 87b is provided with an orientation detection mark, for example, a dot mark, in addition to the horizontal axis 85a and the vertical axis 85b so as to accurately obtain the tilt angle of the test chart image 35b.

When the test chart image 35b is positionally and rotationally displaced from the reference position and the reference orientation, it is necessary to correct the rotational displacement correction prior to measurement of the positional displacement amount (the numbers of pixels in the width Xp and the width Yp). For this reason, unlike the second embodiment, the measurement and correction of the rotational displacement are performed first.

Figure 14A:
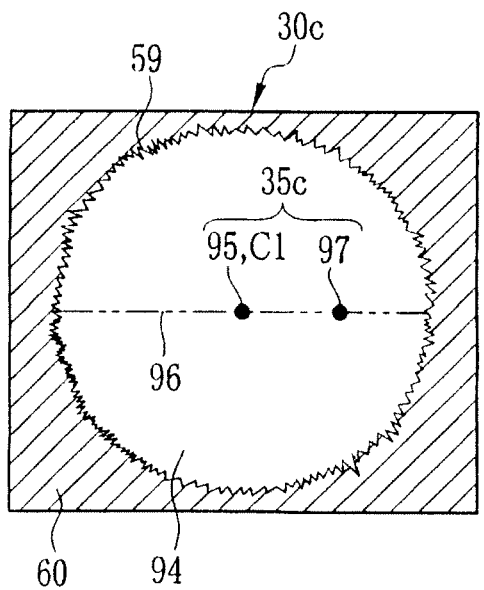
FIG. 14A is an explanatory view of a test chart image of a still another embodiment.
Figure 14B:
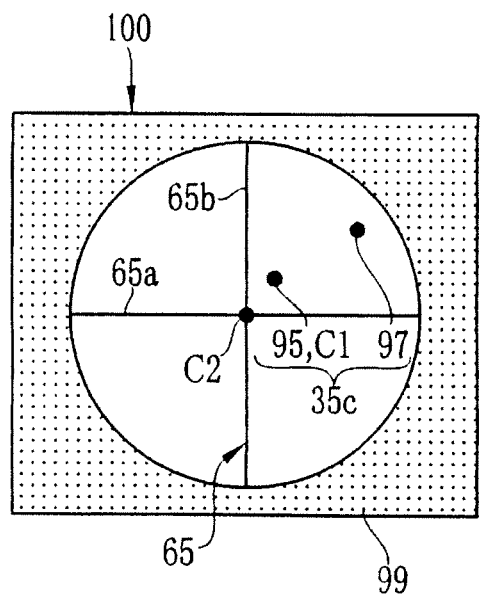
FIG. 14B is an explanatory view illustrating measurement of the positional and rotational displacement amounts of the test mask composite image.

In the third embodiment, the test chart image and the test mask image other than those illustrated in FIGS. 13A to 13D, for example, the test chart image 35c and the test mask image 99 shown in FIGS. 14A and 14B can be used. An endoscope image 30c displays an observation image 94 containing a test chart image 35c. The test chart image 35c consists of a red dot mark 95 indicating the center C1 of the test chart image 35c and a green dot mark 97 indicating orientation of the test chart image 35c. Hereinafter, the red dot mark 95 may be referred to as R dot mark 95, and the green dot mark 97 may be referred to as G dot mark 97. The G dot mark 97 is provided on a virtual horizontal axis 96 (chain double-dashed line) passing the R dot mark 95. The R dot mark 95 and the G dot mark 97 have the same size, and correspond to the chart alignment mark and the orientation detection mark of the present invention, respectively.

As shown in FIG. 14B, a test mask image 99 is the same as the test mask image 57 of the first embodiment except that the scale lines 68 shown in FIG. 5B is not provided. The image compositor 53 composites the test mask image 99 and the endoscope image 30c such that the test mask image 99 is overlaid on the endoscope image 30c to generate a test mask composite image 100, and outputs the test mask composite image 100 to the displacement amount measuring section 82.

The displacement amount measuring section 82 performs image analysis of the test mask composite image 100 to detect the two dot marks 95 and 97 in the test mark composite image 100. Then, the displacement amount measuring section 82 reads the colors of the dot marks 95 and 97 to discriminate between the R dot mark 95 and the G dot mark 97. Thus, the positions of the R dot mark 95 and the G dot mark 97 are detected.

Thereafter, as described in the third embodiment, the displacement amount measuring section 82 measures the numbers of pixels by which the R dot mark 95 is displaced from the center C2 (the origin) of the test mask image 99 in the horizontal and vertical directions of the monitor screen. Thereby, the horizontal displacement amount A and the vertical displacement amount B of the test chart image 35c are obtained.

The displacement amount measuring section 82 measures the numbers of pixels by which the G dot mark 97 is displaced from the center C2 of the test mask image 99 in the horizontal and vertical directions of the monitor screen. Thereby, the horizontal displacement amount Ap and the vertical displacement amount Bp of the G dot mark 97 are obtained. Then, using the mathematical expression (3) described in the third embodiment, the displacement amount measuring section 82 calculates a tilt angle θ between the horizontal line 65a (the X-axis) and the virtual horizontal axis 96 passing the R dot mark 95 and G dot mark 97. Thus, the tilt angle θ of the test chart image 35c is obtained.

The displacement amount information of the test chart image 35c, that is, the horizontal displacement amount A, the vertical displacement amount B, and the tilt angle θ may be automatically measured by the processing device 81 in the same manner as the third embodiment. The colors of the dot marks 95 and 97 are not limited to red and green as long as they differ from each other. The shapes of the dot marks 95 and 97 are not particularly limited. The dot marks 95 and 97 may differ from each other in shape.

In the first embodiment, to align the distal portion 16c with the proper circumferential position, the distal portion 16c of the electronic endoscope 11 is set in the setting hole 38 of the endoscope alignment mechanism 14 first, and then manually rotated in the circumferential direction. Additionally, jigs may be used for the alignment.

Figure 15:
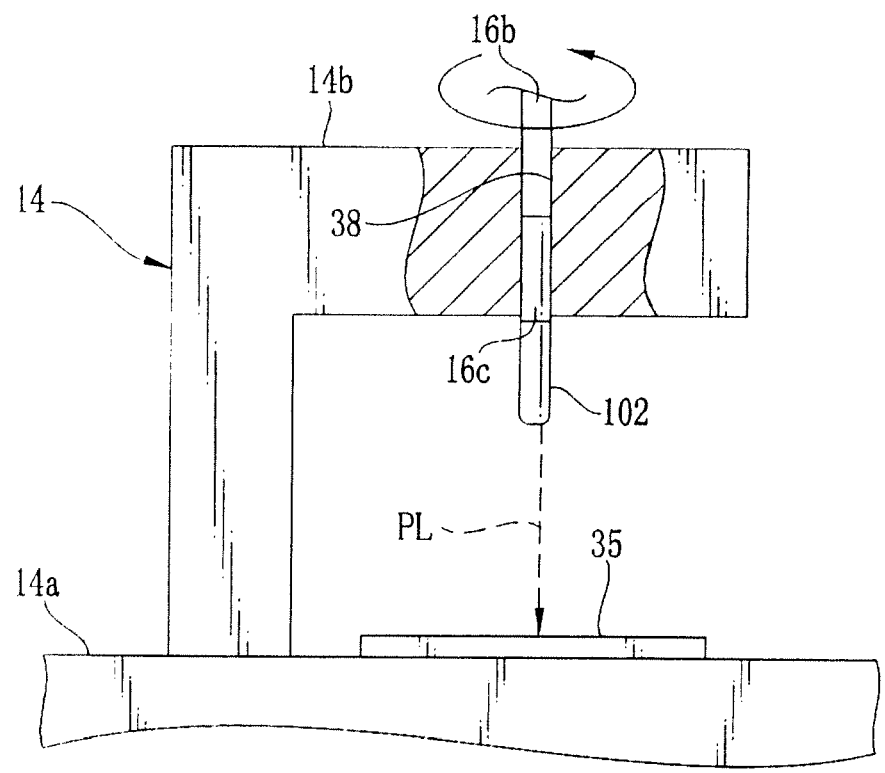
FIG. 15 is an explanatory view illustrating that point light is emitted onto the test chart from a pointer attached to a distal portion of the insert section.
Figure 16B:
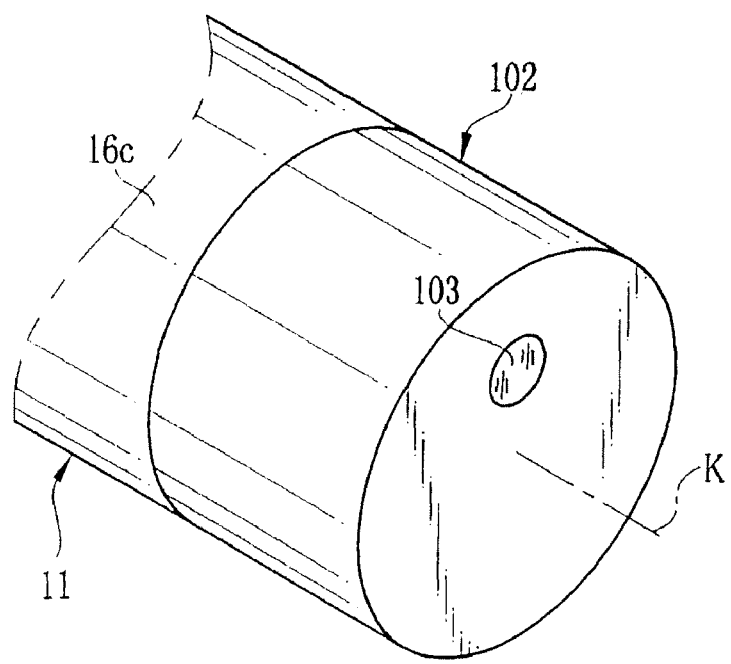
FIG. 16B is a perspective view of the pointer attached to the distal portion.

For example, as shown in FIGS. 15, 16A, and 16B, a pointer 102 is detachably attached to the distal portion 16c set in the setting hole 38. The pointer 102 rotates together with the distal portion 16c when the distal portion 16c is rotated in the circumferential direction. The pointer 102 incorporates a laser emitting device (not shown). The laser emitting device emits a point laser beam PL (illustrated by a dotted line with an arrow) of, for example, 0.5 mm or less in diameter.

In FIG. 16A, the pointer 102 has a cylindrical shape whose diameter is substantially the same as the outer diameter of the distal portion 16c. A front surface of the pointer 102 is provided with an emission window 103 for emitting the point laser beam PL. The emission window 103 is provided in a position off-centered from a rotation axis K of the distal portion 16c.

The back surface of the pointer 102 is provided with metal rods 104a and 104b to position and fix the pointer 102 to the distal portion 16c so that a center axis of the pointer 102 coincides with the rotation axis K of the distal portion 16c. The metal rods 104a and 104b are provided at positions opposing the medical instrument outlet 21, and the air/water nozzle 23 (opening), respectively. The metal rods 104a and 104b have the outer diameters that fit precisely to the medical instrument outlet 21 and the air/water nozzle 23. It should be noted that at least one of the metal rods 104a and 104b is used.

As shown in FIG. 16B, the metal rods 104a and 104b are inserted and fit into the medical instrument outlet 21, and the air/water nozzle 23 respectively. Thus, the pointer 102 is positioned and fixed to the distal portion 16c. Thereafter, when the power of the pointer 102 is turned on, the point laser beam PL is emitted from the emission window 103 to the test chart 35.

Then, the distal portion 16c and the pointer 102 are rotated in the circumferential direction. Since the emission window 103 is off-centered from the rotation axis K, the point laser beam PL lays down a circular trail as it moves on the test chart 35. The position of the emission window 103 or a positioning mark is adjusted such that the point laser beam PL is emitted to the predetermined positioning mark on the test chart 35 when the distal portion 16c reaches the proper circumferential position. For example, the orientation detection mark 37 is used as the positioning mark.

As described above, whether the distal portion 16c is in the proper circumferential position is checked by whether the point laser beam PL is emitted onto the positioning mark on the test chart 35. Thus, the distal portion 16c is surely located to its proper circumferential position. Thereafter, the pointer 102 is removed from the distal portion 16c. Then, the measurement of the displacement amount information and the displacement correction are performed.

In the above embodiments, the distal portion 16c is positioned vertically above the test chart 35 using the endoscope alignment mechanism 14 as an example. Alternatively, the test chart 35 may be positioned in a predetermined position opposing the distal portion 16c.

Figure 17:
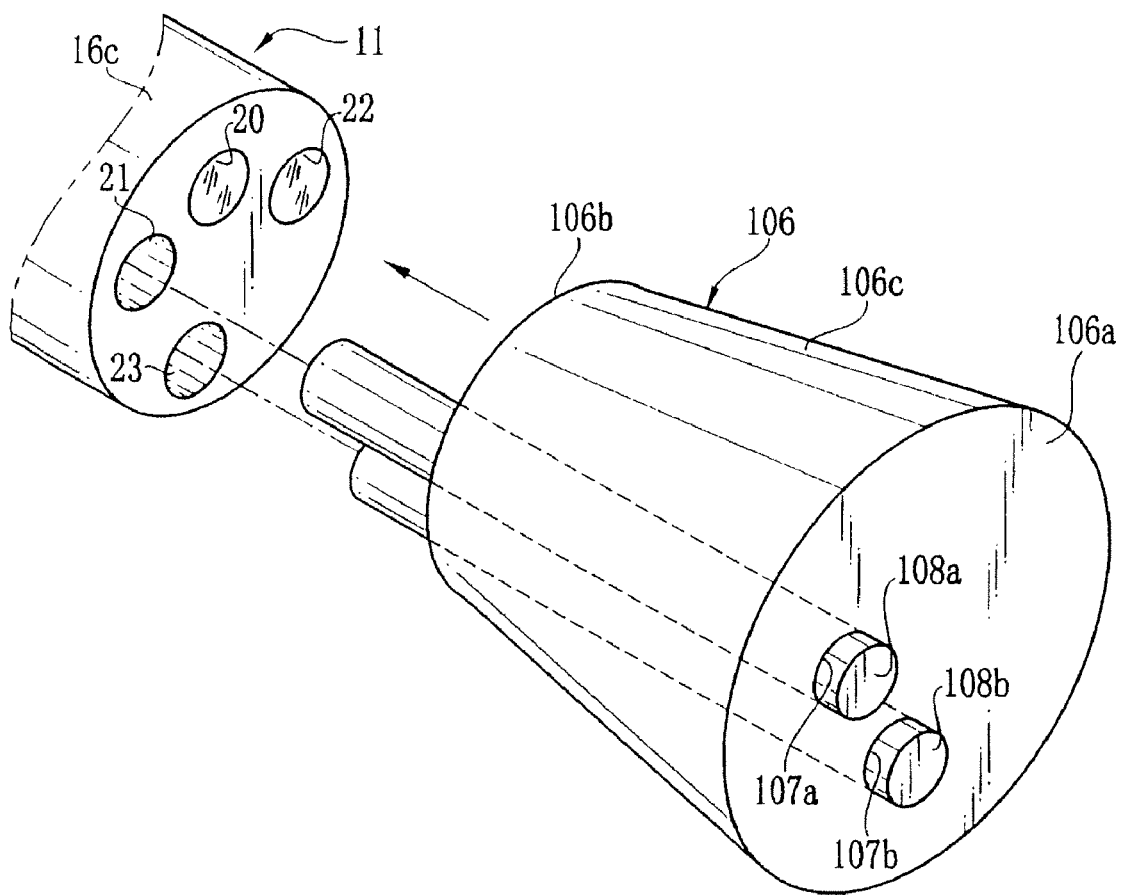
FIG. 17 is a perspective view of an adaptor jig and metal rods.
Figure 18:
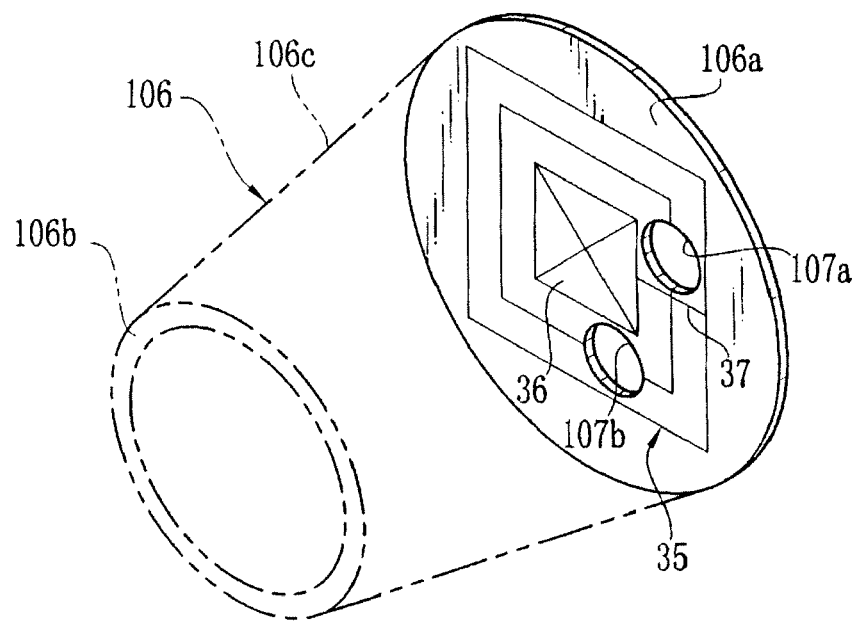
FIG. 18 is a explanatory view of an adaptor jig showing a bottom portion.

As shown in FIGS. 17 and 18, an adaptor jig 106 is detachably attached to the distal portion 16c. The adaptor jig 106 is approximately cup-shaped. The adaptor jig 106 has a bottom portion 106a, an opening 106b, and a tubular portion 106c. The bottom portion 106a opposes the distal portion 16c. The opening 106b fits around the rim of the distal portion 16c. The tubular portion 106c extends between the bottom portion 106a and the opening 106b.

The bottom portion 106a corresponds to the flat stage 14a of the first embodiment. The test chart 35 is provided on an inner surface of the bottom portion 106a, opposing the distal portion 16c. Two through holes 107a and 107b are formed through the bottom portion 106a. When the adaptor jig 106 is attached to the distal portion 16c in a predetermined position, the through hole 107a opposes the medical instrument outlet 21 of the distal portion 16c, and the through hole 107b opposes the air/water nozzle 23. The predetermined position is where the test chart image 35a displayed on the monitor screen satisfies the conditions (1) and (2) described in the first embodiment. The through hole 107a has the same diameter as the medical instrument outlet 21. The through hole 107b has the same diameter as the air/water nozzle 23.

An end portion of a substantially cylindrical positioning rod 108a fits into the through hole 107a, and an end portion of a substantially cylindrical positioning rod 108b fits into the through hole 107b. The other end portion of the positioning rod 108a fits precisely into the medical instrument outlet 21. The other end portion of the positioning rod 108b fits precisely into the air/water nozzle 23. Thereby, the adaptor jig 106 with the test chart 35 is positioned in the predetermined position relative to the distal portion 16c. It should be noted that only at least one of the positioning rods 108a and 108b may be used.

Figure 19:
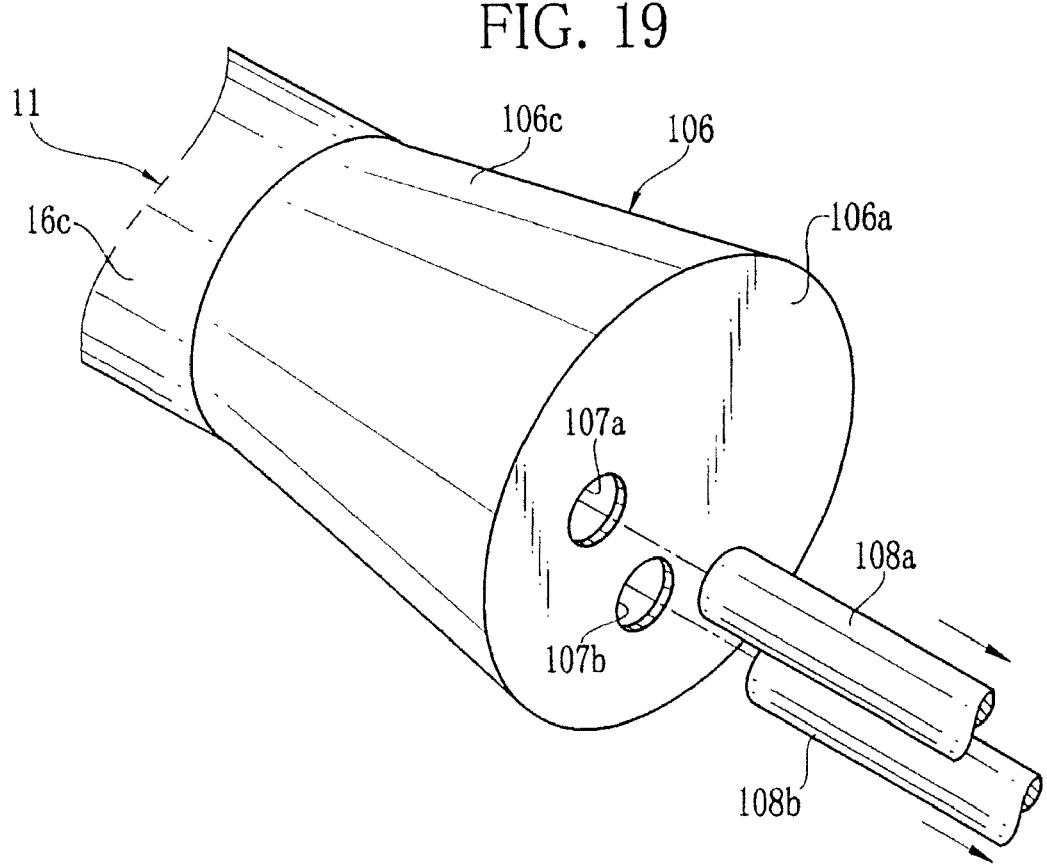
FIG. 19 is an explanatory view illustrating that the metal rods are removed from the adaptor jig.

As shown in FIG. 19, the positioning rods 108a and 108b become obstacles in taking an image of the test chart 35. Therefore, the positioning rods 108a and 108b are removed from the adaptor jig 106 and the distal portion 16c after the positioning of the adaptor jig 106. Before removing the positioning rods 108a and 108b, the inspector detachably fixes the adaptor jig 106 to the distal portion 16c. Means and methods for fixing the adaptor jig 106 to the distal portion 16c are not limited as long as the removal of the positioning rods 108a and 108b is possible. For example, an adhesive tape or a specific fixing jig may be used. A retainer for detachably retaining the adaptor jig 106 may be provided to the distal portion 16c. The opening 106b of the adaptor jig 106 may fit into the distal portion 16c.

After the adaptor jig 106 is positioned and fixed, and the positioning rods 108a and 108b are removed, an image of the test chart 35 is taken. Then, positional and rotational displacement amounts are measured and calibration is performed as described in the first embodiment and the like. It should be noted that the shape of the adaptor jig 106 is not limited to those shown in FIGS. 17 to 19. The shapes of the bottom portion 106a, the opening 106b, and the tubular portion 106c may be changed as necessary.

The chart alignment mark 36 and the orientation detection mark 37 described in the first embodiment are not limited to those shown in FIG. 2, and may be changed to various shapes.

In the above embodiments, examples in which the reference position and the reference orientation of the test chart image 35a satisfy the conditions (1) and (2) are described. These conditions may be changed as necessary. It should be noted, however, the rotational displacement amount is expressed as a tilt angle θ of the orientation detection mark 37 with respect to the X-axis (horizontal line 65a) by defining the reference orientation of the test chart image 35a as the condition (2). Thereby, the rotational displacement amount is easily calculated using the mathematical expressions (1) to (3).

In the above embodiments, examples in which the displacement amount information is stored in the EEPROM 44 of the electronic endoscope 11 are described. Alternatively, the displacement amount information may be stored in a memory of the processing device 12. In this case, the displacement amount information is associated with the identification information of the electronic endoscope 11 and stored in the memory. The CPU 46 retrieves the displacement amount information corresponding to the identification information input from the electronic endoscope 11, and outputs the retrieved displacement amount information to the displacement correction circuit 54. The displacement amount information may be stored in an external memory device, for example, a networked memory device, other than the electronic endoscope and the processing device. The test mask images may also be stored in the external memory device.

In the first embodiment, the inspector visually measures the positional displacement amounts a1 and b1 of the test chart image 35a using the scale lines 68, and the positional displacement amounts a1 and b1 (position coordinates) are converted into positional displacement amounts A and B of pixel numbers. Alternatively, the positional displacement amounts (position coordinates) may be input and converted into the pixel numbers by the processing device 12.

In the above embodiments, the displacement amounts of the test chart image is obtained using the same processing device as that used in the hospital as an example. Alternatively, a device specifically designed for measuring the displacement amounts may be used. The positional displacements may occur with time. In that case, the displacement amounts may be obtained using the processing device in the hospital.

Various changes and modifications are possible in the present invention and may be understood to be within the present invention.

What is claimed is:

1. An apparatus for measuring a displacement amount of an endoscope image, comprising:
    a test chart having a test pattern;
    an alignment section for aligning one of a distal portion of an insert section of an electronic endoscope and said test chart with the other such that said distal portion opposing said test chart and being located in a predetermined circumferential position, said distal portion being inserted into a body cavity;
    an image compositor for generating a composite image from a test pattern image and a reference image having a reference pattern, said test pattern image being obtained by taking an image of said test chart with said electronic endoscope after said alignment, said reference pattern indicating a reference position and a reference orientation of said test pattern; and
    a displacement amount obtaining section for obtaining a displacement amount of said test pattern with respect to said reference pattern in said composite image as said displacement amount of said endoscope image,
    wherein said reference image comprises a mask image for hiding a useless area of said endoscope image, and said mask image includes an unmasked area to expose an area of said endoscope image other than said useless area, and said reference pattern is provided in said unmasked area.

2. The apparatus of claim 1, wherein said test pattern has a chart alignment mark indicating at least one point on said test chart, and an orientation detection mark for detecting an orientation of said test chart, and said reference pattern has a reference position mark indicating at least one point on said reference image and a reference orientation mark, and said reference position mark coincides with said chart alignment mark when said displacement amount is zero, and said reference orientation mark overlaps with said orientation detection mark when said displacement amount is zero, and said displacement amount obtaining section obtains a positional displacement amount and a rotational displacement amount as said displacement amount, and said positional displacement amount comprises a distance between said chart alignment mark and said reference position mark, and said rotational displacement amount comprises an angle between a first line and a second line, and said first line passes said chart alignment mark and said orientation detection mark, and said second line passes said reference position mark and said reference orientation mark.

3. The apparatus of claim 2, wherein said test pattern comprises a checkered pattern of at least two colors arranged alternately, and said chart alignment mark comprises an intersection point of blocks in said checkered pattern, and said orientation detection mark comprises a line of one of said blocks.

4. The apparatus of claim 3, wherein said displacement amount obtaining section reads said colors of said blocks in said composite image, and detects an area of each said color, and automatically measures said displacement amount based on said intersection point of said blocks, said line of one of said blocks, and positions of said reference position mark and said reference orientation mark.

5. The apparatus of claim 2, wherein said chart alignment mark comprises a first dot of a first color, and said orientation detection mark comprises a second dot of a second color different from said first color.

6. The apparatus of claim 5, wherein said displacement amount obtaining section reads said first color and said second color in said composite image and detects positions of said first dot and said second dot based on said reading, and automatically measures said displacement amount based on positions of said first dot, said second dot, said reference position mark and said reference orientation mark.

7. The apparatus of claim 2, wherein said reference image has a scale line to obtain virtual position coordinates of said chart alignment mark and said orientation detection mark in said composite image.

8. The apparatus of claim 7 further including:
a display section for displaying said composite image; and
an input terminal for inputting said position coordinates or said displacement amount calculated from said position coordinates, said displacement amount obtaining section obtaining said position coordinates or said displacement amount input through said input terminal.

9. The apparatus of claim 2, wherein said displacement amount obtaining section analyzes said composite image and obtains said displacement amount by automatic measurement.

10. The apparatus of claim 2, wherein said chart alignment mark indicates a center position of said test chart, and said reference position mark indicates a center position of said reference image.

11. The apparatus of claim 2 further including a displacement correcting section for correcting said displacement of said endoscope image to reduce said displacement amount obtained by said displacement amount obtaining section to zero.

12. The apparatus of claim 11, wherein said displacement amount obtaining section obtains said angle, after said displacement amount obtaining section obtains said positional displacement amount and said displacement correcting section reduces said positional displacement amount to zero.

13. The apparatus of claim 2 further including a displacement amount outputting section for outputting said displacement amount, obtained by said displacement amount obtaining section, to an external memory device.

14. The apparatus of claim 1, wherein said alignment section further includes:
a stage onto which said test chart is placed;
an approximately L-shaped holder attached to said stage; and
a setting hole formed through said holder, said distal portion being inserted into said setting hole, said setting hole rotatably holding said distal portion such that a center of an image sensor of said endoscope and a center of said test pattern coincide with each other when said image sensor is in a correct mounting location.

15. The apparatus of claim 14 further including:
a pointer detachably attached to said distal portion and insertable in said setting hole, said pointer projecting point light along a virtual circle around a center axis of said distal portion, a positioning mark being formed on said test chart, said point light being aligned with said positioning mark when said pointer is rotated together with said distal portion in said setting hole.

16. An electronic endoscope comprising:
a memory for storing said displacement amount obtained by said displacement amount obtaining section of said apparatus for measuring said displacement amount of said endoscope image of claim 2.

17. An image processing device comprising:
a displacement correcting section for retrieving said displacement amount from said memory of said electronic endoscope of claim 16, and performing displacement correction to said endoscope image.

18. An apparatus for measuring a displacement amount of an endoscope image, comprising:
a test chart having a test pattern;
an alignment section for aligning one of a distal portion of an insert section of an electronic endoscope and said test chart with the other such that said distal portion opposing said test chart and being located in a predetermined circumferential position, said distal portion being inserted into a body cavity;
an image compositor for generating a composite image from a test pattern image and a reference image having a reference pattern, said test pattern image being obtained by taking an image of said test chart with said electronic endoscope after said alignment, said reference pattern indicating a reference position and a reference orientation of said test pattern; and
a displacement amount obtaining section for obtaining a displacement amount of said test pattern with respect to said reference pattern in said composite image as said displacement amount of said endoscope image,
wherein said alignment section further includes:
a tube-like adaptor detachably attached to said distal portion, said adaptor having an opening opposing said distal portion, a bottom portion positioned opposite to said opening, and at least one through hole formed through said bottom portion, said test chart being attached to inside of said bottom portion; and
a rod inserted through said through hole, an end of said rod being inserted into an opening of said distal portion, said rod being removed from said through hole after said adapter is attached to said distal portion.

19. A method for measuring a displacement amount of an endoscope image, said method comprising:
aligning a first one of a distal portion of an insert section of an electronic endoscope and a test chart with a second one thereof such that said distal portion opposing said test chart and being located in a predetermined circumferential position, said test chart having a test pattern, said distal portion being inserted into a body cavity;
generating a composite image from a test pattern image and a reference image having a reference pattern, said test pattern image being obtained by taking an image of said test chart with said electronic endoscope after said alignment, said reference pattern indicating a reference position and a reference orientation of said test pattern; and
obtaining a displacement amount of said test pattern with respect to said reference pattern in said composite image as said displacement amount of said endoscope image,
wherein said reference image comprises a mask image for hiding a useless area of said endoscope image, and said mask image includes an unmasked area to expose an area of said endoscope image other than said useless area, and said reference pattern is provided in said unmasked area.

* * * * *